United States Patent
Steinmetz et al.

(10) Patent No.: US 12,376,711 B2
(45) Date of Patent: Aug. 5, 2025

(54) PRODUCT DISPENSER HOLDER WITH COMPLIANCE MODULE

(71) Applicant: Ecolab USA Inc., St. Paul, MN (US)

(72) Inventors: Nicholas Joseph Steinmetz, St Paul, MN (US); Jeffrey Rospierski, Alden, NY (US); Sarah E. Johnson, St Paul, MN (US); Viktor Slobodyan, Burnsville, MN (US); David L. Snodgrass, Stuart, FL (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

(21) Appl. No.: 18/439,111

(22) Filed: Feb. 12, 2024

(65) Prior Publication Data

US 2024/0180369 A1    Jun. 6, 2024

Related U.S. Application Data

(63) Continuation of application No. 18/182,810, filed on Mar. 13, 2023, now Pat. No. 11,918,158, which is a
(Continued)

(51) Int. Cl.
*A47K 5/12* (2006.01)
*B05B 12/00* (2018.01)
*B05B 15/62* (2018.01)

(52) U.S. Cl.
CPC .......... *A47K 5/1217* (2013.01); *A47K 5/1205* (2013.01); *B05B 12/004* (2013.01);
(Continued)

(58) Field of Classification Search
CPC .......... A47K 5/1217; A47K 2005/1218; A47K 2201/00; A47K 2201/02; G08B 21/245; G09B 19/0076
See application file for complete search history.

(56) References Cited

U.S. PATENT DOCUMENTS

| | | |
|---|---|---|
| 2,883,139 A | 4/1959 | Dobkin |
| 3,032,081 A | 5/1962 | Cotta |

(Continued)

FOREIGN PATENT DOCUMENTS

| | | |
|---|---|---|
| WO | WO-2011131800 A1 | 10/2011 |
| WO | WO-2022159378 A1 | 7/2022 |

OTHER PUBLICATIONS

U.S. Appl. No. 17/648,248 U.S. Pat. No. 11,602,248, filed Jan. 18, 2022, Product Dispenser Holder With Compliance Module.
(Continued)

*Primary Examiner* — Vishal Pancholi
(74) *Attorney, Agent, or Firm* — Schwegman Lundberg & Woessner, P.A.

(57) ABSTRACT

A product dispenser holder comprises a dispenser holder body configured to receive a product dispenser that stores a supply of a product to be dispensed, an actuation sensor that senses actuations of the product dispenser, and an actuation button, such that when an actuation force is applied to a pump of the product dispenser, a substantially downward force is applied to the actuation button causing the actuation button to rotate substantially downwardly and actuate the actuation sensor to generate a dispenser actuation signal.

20 Claims, 12 Drawing Sheets

Related U.S. Application Data continuation of application No. 17/648,248, filed on Jan. 18, 2022, now Pat. No. 11,602,248.

(60) Provisional application No. 63/139,634, filed on Jan. 20, 2021.

(52) U.S. Cl.
CPC ...... *B05B 15/62* (2018.02); *A47K 2005/1218* (2013.01); *A47K 2201/00* (2013.01); *A47K 2201/02* (2013.01)

(56) References Cited

U.S. PATENT DOCUMENTS

| | | | |
|---|---|---|---|
| 3,033,404 A | 5/1962 | Adell | |
| 3,198,437 A | 8/1965 | Faglie | |
| 4,164,306 A | 8/1979 | Perrin | |
| 4,166,553 A | 9/1979 | Fraterrigo | |
| 4,185,759 A | 1/1980 | Zissimopoulos | |
| 4,240,129 A | 12/1980 | Kawazoe | |
| 4,461,445 A | 7/1984 | Williamson et al. | |
| 4,504,168 A | 3/1985 | Miller | |
| 4,561,571 A | 12/1985 | Chen | |
| 4,997,157 A | 3/1991 | Sweeny | |
| 5,350,087 A | 9/1994 | Frazier et al. | |
| 5,435,511 A | 7/1995 | Hsu | |
| 5,449,137 A | 9/1995 | Bell et al. | |
| 5,638,989 A | 6/1997 | Ophardt et al. | |
| 5,992,698 A | 11/1999 | Copeland et al. | |
| 6,131,773 A | 10/2000 | Wade et al. | |
| 6,209,184 B1 | 4/2001 | Copeland et al. | |
| 6,540,119 B1 | 4/2003 | Bensussan et al. | |
| 6,575,335 B2 | 6/2003 | Lewis et al. | |
| 6,609,679 B1 | 8/2003 | Seidel | |
| 6,637,707 B1 | 10/2003 | Gates et al. | |
| 6,820,770 B2 | 11/2004 | Makino et al. | |
| 7,090,085 B1 | 8/2006 | Vicendese et al. | |
| 7,104,467 B2 | 9/2006 | Crossdale et al. | |
| D533,742 S | 12/2006 | Matthews et al. | |
| 7,254,895 B1 | 8/2007 | Odonnell | |
| 7,275,729 B2 | 10/2007 | Sherman et al. | |
| 7,290,683 B2 | 11/2007 | Gerenraich | |
| 7,315,245 B2 | 1/2008 | Lynn et al. | |
| 7,375,640 B1 | 5/2008 | Plost | |
| 7,404,534 B1 | 7/2008 | Hajianpour | |
| 7,423,533 B1 | 9/2008 | Leblond et al. | |
| 7,654,321 B2 | 2/2010 | Zazovsky et al. | |
| 7,793,902 B2 | 9/2010 | Buchanan et al. | |
| 7,857,170 B2 | 12/2010 | Ophardt | |
| 8,030,940 B2 | 10/2011 | Nishimoto | |
| 8,096,445 B2 | 1/2012 | Yang et al. | |
| 8,100,299 B2 | 1/2012 | Phelps et al. | |
| 8,169,327 B2 | 5/2012 | Lynn | |
| 8,230,888 B2 | 7/2012 | Crossdale et al. | |
| 8,240,517 B1 | 8/2012 | Stob et al. | |
| 8,286,835 B2 | 10/2012 | Morey et al. | |
| 8,350,706 B2 | 1/2013 | Wegelin et al. | |
| 8,395,515 B2 | 3/2013 | Tokhtuev et al. | |
| 8,407,018 B2 | 3/2013 | White et al. | |
| 8,489,348 B2 | 7/2013 | Shirriff et al. | |
| 8,502,680 B2 | 8/2013 | Tokhtuev et al. | |
| 8,558,701 B2 | 10/2013 | Archer et al. | |
| 8,598,848 B2 | 12/2013 | Zheng et al. | |
| 8,603,014 B2 | 12/2013 | Alleman et al. | |
| 8,616,511 B2 | 12/2013 | James | |
| 8,631,843 B2 | 1/2014 | O'brien | |
| 8,668,178 B2 | 3/2014 | Ziaylek et al. | |
| 8,731,622 B2 | 5/2014 | Kanade et al. | |
| 8,751,845 B2 | 6/2014 | Assad et al. | |
| 8,757,573 B1 | 6/2014 | Barnes, Jr. | |
| 8,766,643 B2 | 7/2014 | Thoren et al. | |
| 8,783,511 B2 | 7/2014 | Snodgrass | |
| 8,816,860 B2 | 8/2014 | Ophardt et al. | |
| 8,844,769 B2 | 9/2014 | Rosenkranz et al. | |
| 8,965,595 B2 | 2/2015 | Wegelin | |
| 9,078,936 B1 | 7/2015 | Denby, Jr. | |
| 9,117,361 B1 | 8/2015 | Hennigan et al. | |
| 9,123,233 B2 | 9/2015 | Hermann | |
| 9,131,811 B2 | 9/2015 | Wegelin et al. | |
| 9,144,160 B2 | 9/2015 | Chuang | |
| D777,020 S | 1/2017 | Zlatic et al. | |
| 9,770,141 B2 | 9/2017 | Wegelin et al. | |
| 10,039,423 B2 | 8/2018 | Schultz et al. | |
| 10,667,654 B2 | 6/2020 | Schultz et al. | |
| 11,253,109 B2 | 2/2022 | Schultz et al. | |
| RE48,951 E | 3/2022 | Bryant et al. | |
| 11,602,248 B2 * | 3/2023 | Steinmetz | F16M 11/08 |
| 11,918,158 B2 | 3/2024 | Steinmetz et al. | |
| 2001/0054626 A1 | 12/2001 | Bethune et al. | |
| 2002/0100676 A1 | 8/2002 | Janniere | |
| 2004/0150527 A1 | 8/2004 | Harper et al. | |
| 2005/0282142 A1 | 12/2005 | Lynn et al. | |
| 2006/0043051 A1 | 3/2006 | Bissett | |
| 2006/0067545 A1 | 3/2006 | Lewis et al. | |
| 2006/0067546 A1 | 3/2006 | Lewis et al. | |
| 2006/0071799 A1 | 4/2006 | Verdiramo | |
| 2006/0081749 A1 | 4/2006 | Sherman et al. | |
| 2006/0175341 A1 | 8/2006 | Rodrian | |
| 2006/0186140 A1 | 8/2006 | Kanfer et al. | |
| 2006/0273915 A1 | 12/2006 | Snodgrass | |
| 2007/0229288 A1 | 10/2007 | Ogrin et al. | |
| 2008/0019490 A1 | 1/2008 | Lynn | |
| 2008/0087719 A1 | 4/2008 | Sahud | |
| 2008/0131332 A1 | 6/2008 | Nguyen et al. | |
| 2008/0290112 A1 | 11/2008 | Lynn | |
| 2008/0302440 A1 | 12/2008 | Crossdale et al. | |
| 2009/0051545 A1 | 2/2009 | Koblasz | |
| 2009/0068116 A1 | 3/2009 | Arndt | |
| 2009/0166378 A1 | 7/2009 | Stilley | |
| 2009/0166381 A1 | 7/2009 | Phelps et al. | |
| 2009/0195385 A1 | 8/2009 | Huang et al. | |
| 2009/0289163 A1 | 11/2009 | Morey et al. | |
| 2009/0299787 A1 | 12/2009 | Barnhill | |
| 2010/0094581 A1 | 4/2010 | Cagle | |
| 2010/0153374 A1 | 6/2010 | Leblond et al. | |
| 2010/0164728 A1 | 7/2010 | Plost | |
| 2010/0207767 A1 | 8/2010 | Verdiramo | |
| 2010/0212778 A1 | 8/2010 | Obrien | |
| 2010/0315243 A1 | 12/2010 | Tokhtuev et al. | |
| 2010/0328076 A1 | 12/2010 | Kyle et al. | |
| 2010/0332022 A1 | 12/2010 | Wegelin et al. | |
| 2011/0024585 A1 | 2/2011 | Brinkdopke et al. | |
| 2011/0030730 A1 | 2/2011 | Lynn | |
| 2011/0046921 A1 | 2/2011 | Sahud | |
| 2011/0088809 A1 | 4/2011 | Lin | |
| 2011/0093313 A1 | 4/2011 | Leblond et al. | |
| 2011/0163870 A1 | 7/2011 | Snodgrass | |
| 2011/0180564 A1 | 7/2011 | Jones et al. | |
| 2011/0234407 A1 | 9/2011 | Harris et al. | |
| 2011/0259920 A1 | 10/2011 | Rennie et al. | |
| 2011/0273298 A1 | 11/2011 | Snodgrass et al. | |
| 2011/0316701 A1 | 12/2011 | Alper et al. | |
| 2011/0320134 A1 | 12/2011 | Butler et al. | |
| 2012/0055986 A1 | 3/2012 | Sahud | |
| 2012/0112914 A1 | 5/2012 | Wegelin et al. | |
| 2012/0181405 A1 | 7/2012 | Zlatic et al. | |
| 2012/0187146 A1 | 7/2012 | Chopra | |
| 2012/0218106 A1 | 8/2012 | Zaima et al. | |
| 2012/0245729 A1 | 9/2012 | Wegelin et al. | |
| 2012/0256742 A1 | 10/2012 | Snodgrass et al. | |
| 2012/0274468 A1 | 11/2012 | Wegelin et al. | |
| 2012/0317432 A1 | 12/2012 | Assad et al. | |
| 2012/0329438 A1 | 12/2012 | Snodgrass | |
| 2013/0009027 A1 | 1/2013 | Morey et al. | |
| 2013/0025714 A1 | 1/2013 | Hermann | |
| 2013/0027199 A1 | 1/2013 | Bonner | |
| 2013/0043284 A1 | 2/2013 | Wegelin et al. | |
| 2013/0048142 A1 | 2/2013 | Crossdale et al. | |
| 2013/0075346 A1 | 3/2013 | Rumberger et al. | |
| 2013/0076514 A1 | 3/2013 | Wegelin et al. | |
| 2013/0087579 A1 | 4/2013 | Knighton | |
| 2013/0098941 A1 | 4/2013 | Wegelin | |
| 2013/0099900 A1 | 4/2013 | Pulvermacher | |

(56) References Cited

U.S. PATENT DOCUMENTS

| | | |
|---|---|---|
| 2013/0113931 A1 | 5/2013 | Alper |
| 2013/0120120 A1 | 5/2013 | Long et al. |
| 2013/0229276 A1 | 9/2013 | Hunter |
| 2013/0261795 A1 | 10/2013 | Long et al. |
| 2013/0264355 A1 | 10/2013 | Jodoin |
| 2013/0264925 A1 | 10/2013 | Kling |
| 2013/0292411 A1 | 11/2013 | Bem |
| 2013/0306105 A1 | 11/2013 | Battah |
| 2013/0323003 A1 | 12/2013 | Carson |
| 2014/0015670 A1 | 1/2014 | Wegelin et al. |
| 2014/0076938 A1 | 3/2014 | Bonner et al. |
| 2014/0081653 A1 | 3/2014 | Davis et al. |
| 2014/0091926 A1 | 4/2014 | Gips et al. |
| 2014/0158714 A1 | 6/2014 | Snodgrass et al. |
| 2014/0197194 A1 | 7/2014 | Wegelin et al. |
| 2014/0311239 A1 | 10/2014 | Marjanovic et al. |
| 2015/0022361 A1 | 1/2015 | Gaisser et al. |
| 2015/0061867 A1 | 3/2015 | Engelhard et al. |
| 2015/0083754 A1 | 3/2015 | Proper et al. |
| 2015/0134357 A1 | 5/2015 | Davis et al. |
| 2015/0199883 A1 | 7/2015 | Hartley et al. |
| 2015/0313422 A1 | 11/2015 | Ophardt et al. |
| 2016/0374519 A1 | 12/2016 | Murphy |
| 2018/0255918 A1 | 9/2018 | Walker |
| 2018/0255981 A1 | 9/2018 | Rospierski et al. |
| 2018/0317717 A1* | 11/2018 | Schultz ................ A47K 5/1205 |
| 2020/0205055 A1 | 6/2020 | Snodgrass |
| 2020/0281416 A1 | 9/2020 | Schultz et al. |
| 2021/0012640 A1 | 1/2021 | Tokhtuev et al. |
| 2022/0142414 A1 | 5/2022 | Schultz et al. |
| 2022/0225845 A1 | 7/2022 | Steinmetz et al. |
| 2023/0210318 A1 | 7/2023 | Steinmetz et al. |

OTHER PUBLICATIONS

U.S. Appl. No. 18/182,810 U.S. Pat. No. 11,918,158, filed Mar. 13, 2023, Product Dispenser Holder With Compliance Module.

* cited by examiner

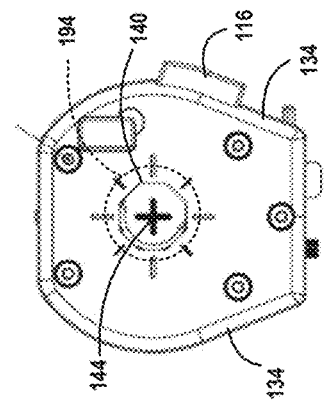
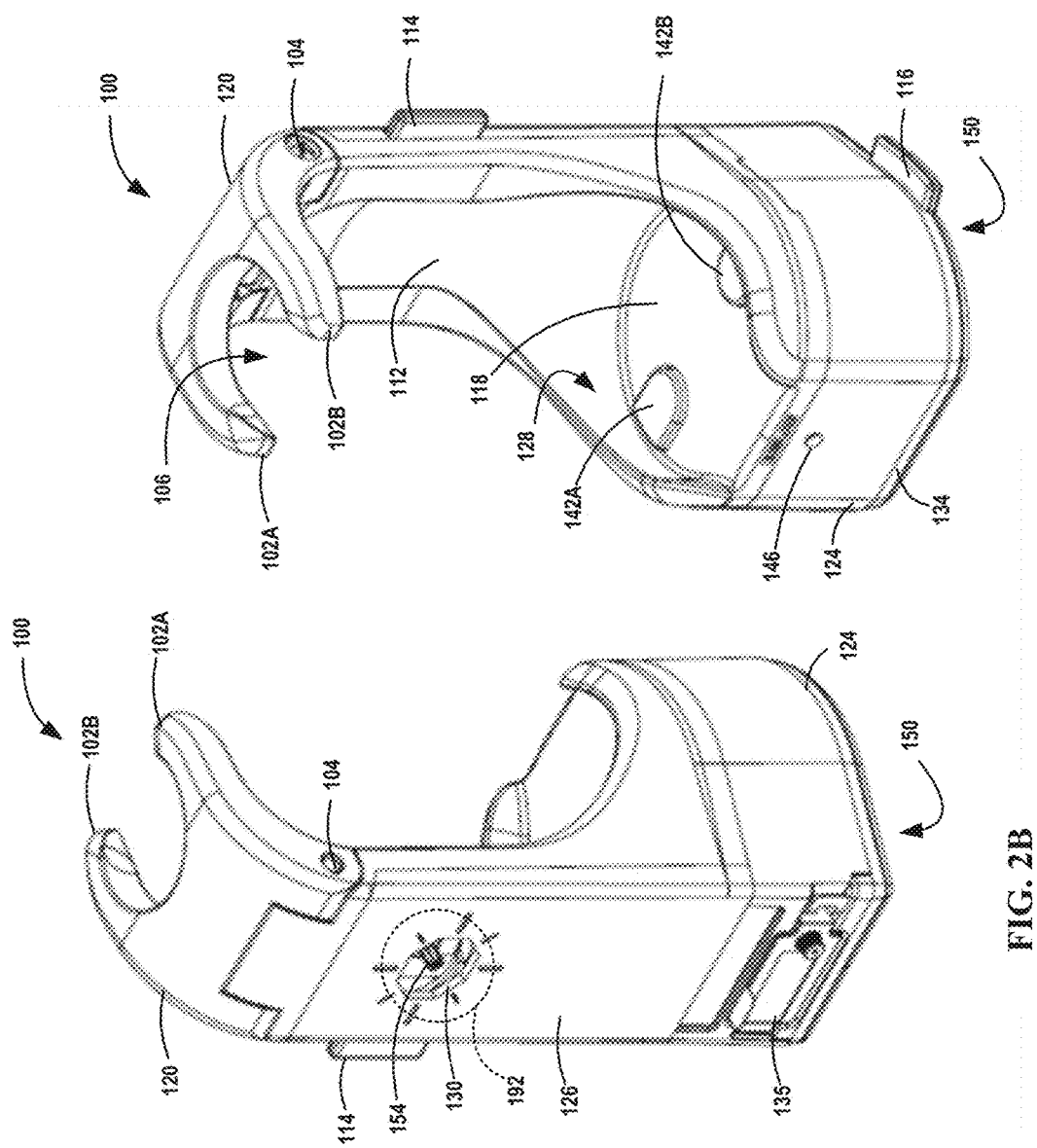
FIG. 2C
FIG. 2A
FIG. 2B

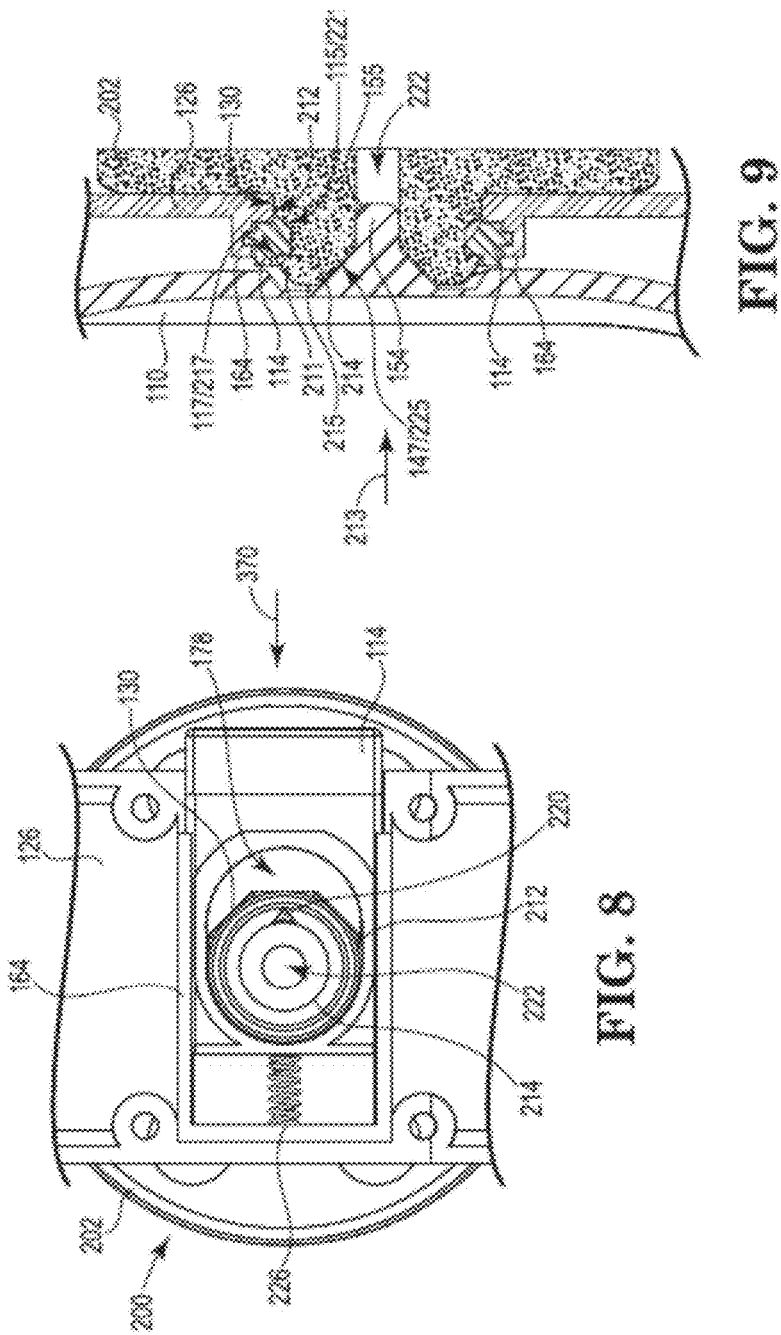

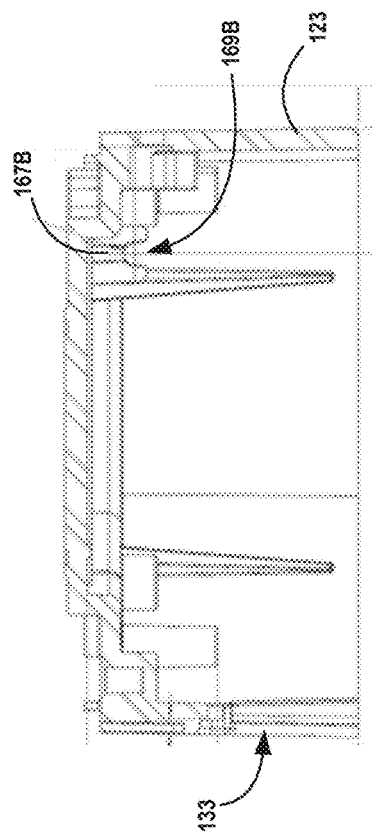
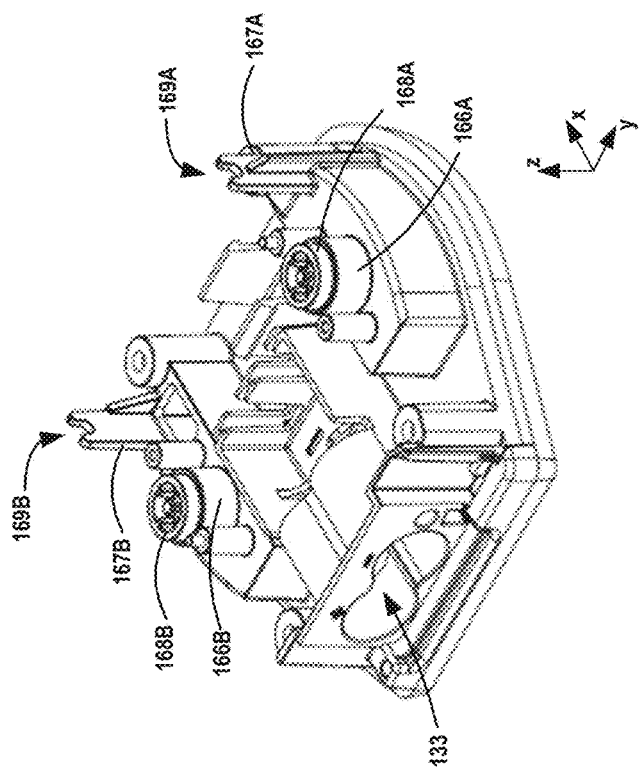
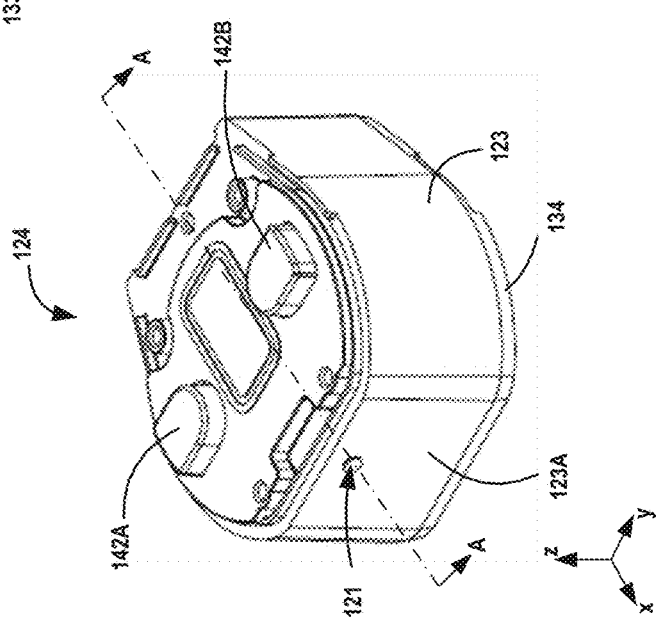
FIG. 10C
FIG. 10D
FIG. 10A

PRODUCT DISPENSER HOLDER WITH COMPLIANCE MODULE

This application is a continuation of U.S. patent application Ser. No. 18/182,810, filed Mar. 13, 2023, which is a continuation of U.S. patent application Ser. No. 17/648,248, filed Jan. 18, 2022, now issued as U.S. Pat. No. 11,602,248, which claims the benefit of U.S. Provisional Patent Application No. 63/139,634, filed Jan. 20, 2021, the entire content of each of which are incorporated by reference herein in their entirety.

BACKGROUND

Product dispensers are used for a variety of purposes and for a variety of applications. For example, hand hygiene product dispensers are often used in health care and food service settings to reduce pathogen transmission that may lead to the spread of illness. Compliance with hand hygiene guidelines is considered the most effective action health care and food service workers can take to reduce pathogen transmission. To facilitate compliance with hand hygiene procedures, hand hygiene product dispensers should be readily available so that hand washing and/or sanitizing is easy and convenient. For example, hand hygiene products, such as liquid, foam, lotion, or gel hand washing soaps and/or sanitizers, may be placed near sinks or other hand washing stations in a healthcare or restaurant setting to facilitate compliance with hand hygiene procedures.

SUMMARY

In general, the disclosure describes a product dispenser holder configured to receive and support a product dispenser. The product dispenser may include, for example, a product reservoir containing a supply of product to be dispensed and a pump that when actuated causes a dosage amount of the product from the reservoir to be dispensed. The dispenser holder includes a compliance module configured to detect each actuation of the product dispenser. The dispenser holder compliance module may further wirelessly communicate dispense event data corresponding to one or more detected actuations of the product dispenser for receipt by one or more computing devices. In some examples, the dispenser holder includes an adjustable mounting mechanism configured to mount the dispenser holder to a variety of different support objects.

In some examples, to detect actuation of the product dispenser, the compliance module includes a controller and a detection mechanism in the base of the dispenser holder that is activated when a dispensing force is applied to the pump of the product dispenser. Detection of the actuation force activates a pump actuation signal that is received by the controller, resulting in detection of actuation of the product dispenser.

In some examples, the product is a hand hygiene product, such as a hand soap or a hand sanitizer. In such examples, the dispense event data transmitted by the compliance module includes hand hygiene compliance data associated with each detected actuation of the product dispenser. The hand hygiene compliance data may be communicated to a hand hygiene compliance system for monitoring and analysis of compliance with hand hygiene procedures.

In one example, the disclosure is directed to a product dispenser holder comprising a dispenser holder body configured to receive a product dispenser, the product dispenser having a product reservoir that stores a supply of a product to be dispensed and a pump in fluid connection with the reservoir, such that when the pump is actuated a dosage amount of the product is dispensed from the product reservoir, the dispenser holder body further including a base having at least one aperture; and a sensor module that senses actuations of the product dispenser, the sensor module further comprising processing circuitry configured to detect a dispense event upon receipt of a dispenser actuation signal, and to generate dispense event data corresponding to the dispense event; an actuation sensor that generates the dispenser actuation signal; and an actuation button comprising a main body portion; at least one cap portion extending upwardly from a top side of the main body portion and sized to extend through the at least one aperture in the base of the dispenser holder body; and at least one hinge pin extending from a first side of the main body portion; such that when an actuation force is applied to the pump of the product dispenser, a substantially downward force is applied to the at least one cap portion of the actuation button extending through the at least one aperture in the base of the dispenser holder body, causing the actuation button to rotate on an axis defined by the at least one hinge pin such that the actuation button rotates substantially downwardly and actuates the actuation sensor to generate the dispenser actuation signal.

In some examples, the product dispenser holder may further comprise a sensor module body forming at least one lower spring seat; wherein the main body portion of the actuation button further at least one upper spring seat on a bottom side of the main body portion; and wherein the at least one cap portion is biased by a spring seated between the lower spring seat and the upper spring seat.

In some examples, the sensor module may further include a counter that increments a dispense event count in response to each detected actuation of the product dispenser. The processing circuitry may further be configured to communicate the dispense event data corresponding to a hand hygiene compliance computing system. The hand hygiene compliance computing system may be configured to analyze the dispense event data received from one or more product dispenser holders in a facility to monitor hand hygiene compliance of one or more workers associated with the facility. The sensor module may be further configured to, in response to detection of a dispenser actuation, communicate with a compliance badge and receive at least one of compliance badge identification information or worker identification information from the compliance badge. The processing circuitry may further be configured to store the dispense event data corresponding to each detected dispense event.

In some examples, the base of the dispenser hold body may further include first and second apertures, and the actuation button may include first and second cap portions extending upwardly from a top side of the main body portion and sized to extend through the first and second apertures in the base of the dispenser holder body, respectively; such that when an actuation force is applied to the product dispenser, a substantially downward force is applied to at least one of the first and second cap portions of the actuation button, causing actuation button to rotate on an axis defined by first and second hinge pins such that actuation tab rotates substantially downwardly and depresses actuation switch to generate the dispenser actuation signal.

In some examples, the sensor module body may form a first lower spring seat and a second lower spring seat, the main body portion of the actuation button may further include a first upper spring seat on the bottom side of the main body portion and a second upper spring seat on the bottom side of the main body portion, and wherein the first cap portion is biased by first spring seated between the first lower spring seat and the first upper spring seat, and the second cap portion is biased by second spring seated between the second lower spring seat and the second upper spring seat.

In some examples, the actuation sensor may include one of a mechanical switch, a reed switch, an accelerometer, a load cell, an optical sensor, a membrane switch, or a capacitive sensor.

In some examples, the actuation button may further comprise an actuation tab extending from a second side of the main body portion, wherein when an actuation force is applied to the pump of the product dispenser, a substantially downward force is applied to the at least one cap portion of the actuation button, causing the actuation button to rotate on the axis defined by the at least one hinge pin such that the actuation tab rotates substantially downwardly and actuates the actuation sensor to generate the dispenser actuation signal.

In another example, the disclosure is directed to a product dispenser holder comprising a dispenser holder body configured to receive a product dispenser, the product dispenser having a product reservoir that stores a supply of a product to be dispensed and a pump in fluid connection with the reservoir, such that when the pump is actuated a dosage amount the product is dispensed from the product reservoir, the dispenser holder body further including a base having at least one aperture; and a sensor module that senses actuations of the product dispenser, the sensor module further comprising processing circuitry configured to detect a dispense event upon receipt of a dispenser actuation signal, and to generate dispense event data corresponding to the dispense event; an actuation sensor that generates the dispenser actuation signal; and an actuation button comprising a main body portion; at least one cap portion extending upwardly from a top side of the main body portion and sized to extend through the at least one aperture in the base of the dispenser holder body; and an actuation tab extending from the main body portion, such that when an actuation force is applied to the pump of the product dispenser, a substantially downward force is applied to the at least one cap portion of the actuation button, causing the actuation tab to rotate substantially downwardly and actuate the actuation sensor to generate the dispenser actuation signal.

The details of one or more examples are set forth in the accompanying drawings and the description below. Other features will be apparent from the description and drawings, and from the claims.

BRIEF DESCRIPTION OF DRAWINGS

FIG. 2A is a front perspective view of the example dispenser holder of FIG. 1, in accordance with one or more aspects of the present disclosure.

FIG. 2B is a back perspective view of an example dispenser holder, in accordance with one or more aspects of the present disclosure.

FIG. 2C is a bottom view of the example dispenser holder of FIG. 1, in accordance with one or more aspects of the present disclosure.

FIG. 8 is an interior view illustrating the fitting of an example mounting bracket 200 and back plate 126 of an example dispenser holder.

FIG. 9 is a side cross-sectional view of an example dispenser holder releasably connected to an example mounting clamp.

FIG. 10A shows a perspective view of an example dispenser holder sensor module, in accordance with one or more aspects of the present disclosure.

FIG. 10C shows a cross-sectional side view of module cover, in accordance with one or more aspects of the present disclosure.

FIG. 10D shows a back perspective view of module body, in accordance with one or more aspects of the present disclosure.

DETAILED DESCRIPTION

Figures 1A, 1B:
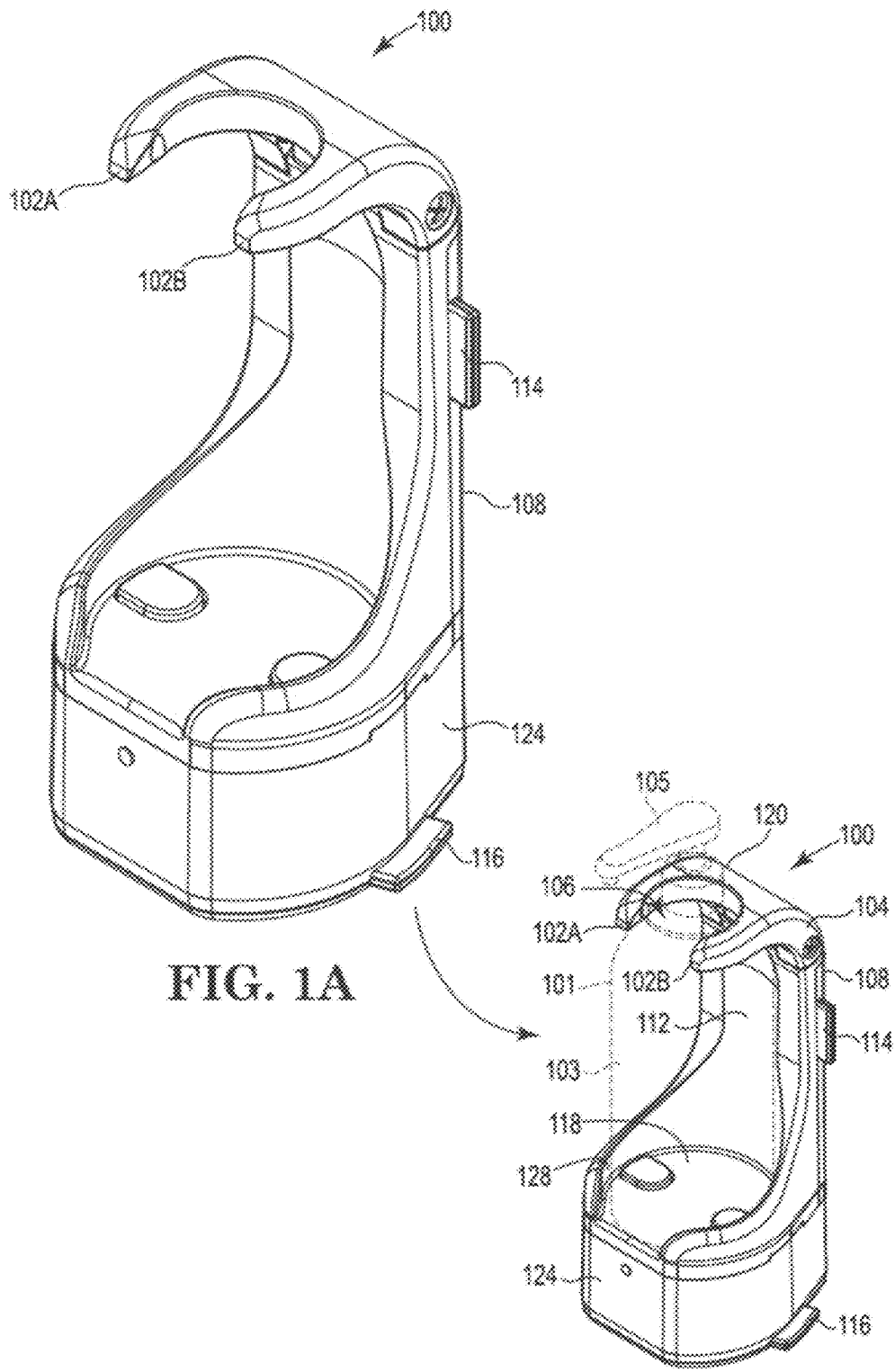
FIG. 1A is a front perspective view of an example dispenser holder and FIG. 1B is a front perspective view of the example dispenser holder having an example product dispenser installed therein, in accordance with one or more aspects of the present disclosure.

In general, the disclosure describes a product dispenser holder configured to receive and support a product dispenser. The product dispenser may include, for example, a product reservoir containing a supply of product to be dispensed and a pump that when actuated causes a dosage amount of the product from the reservoir to be dispensed. The dispenser holder includes a compliance module configured to detect each actuation of the product dispenser ("dispense event"). The dispenser holder compliance module may further wirelessly communicate the dispense event data for receipt by a compliance system. In some examples, the dispenser holder includes an adjustable mounting mechanism configured to mount the dispenser holder to a variety of different support objects.

In some examples, to detect actuation of the product dispenser, the compliance module includes a detection mechanism in the base of the dispenser holder that is activated when a dispensing force is applied to the pump of the product dispenser. Detection of the dispensing force activates a pump actuation signal that is received by the controller, resulting in detection of actuation of the product dispenser.

In some examples, the product is a hand hygiene product, such as a hand soap or a hand sanitizer, and the dispense event data is communicated to a hand hygiene compliance system for monitoring and analysis of compliance with hand hygiene procedures. In some examples, the dispenser holder includes an adjustable mounting mechanism configured to mount the dispenser holder to a variety of different support objects, thus facilitating compliance with hand hygiene procedures and detection of hand hygiene events at the "point of care." In other words, the hand hygiene product dispenser holder enables hand hygiene events to be carried out in close proximity to a patient, meaning the overall time between the hand hygiene event and the patient interaction is reduced.

In some examples, the adjustable mounting apparatus provides for releasable and rotatable attachment of the dispenser holder to the mounting apparatus in multiple orientations while maintaining the product dispenser in a proper dispensing orientation regardless of which way the mounting mechanism is attached to a support object. For example, the mounting apparatus may include a mounting bracket or clamp, and the support object may include any type of flat, curved, or irregular surface, including but not limited to a wall, a table, a counter top, a cabinet, a shelf, a cart, a pole, a mobile workstation, a column, etc.

The product dispenser holder with compliance module according to one or more aspects of the present disclosure may provide several advantages. For example, the product dispenser holder with compliance module detects each actuation of the product dispenser ("dispense event"). The dispenser holder compliance module may further wirelessly communicate the dispense event data corresponding to each detected dispense event for receipt by a compliance system. The dispense event data may be analyzed by the compliance system to monitor dispenser actuations of one or more product dispensers at one or more facilities or locations. For example, the dispense event data may be analyzed by the compliance system in order to monitor compliance with dispensing of one or more product types at a facility or at multiple facilities. For example, the compliance system may be monitor dispenser actuations of one or more hand hygiene product dispensers to monitor compliance with hand hygiene procedures for a facility, such as a hospital, clinic or other healthcare facility, at a restaurant or food processing facility, or at any other facility or location where compliance with hand hygiene procedures is to be monitored. In addition, in a healthcare application, the product dispenser holder facilitates compliance with hand hygiene procedures and detection of hand hygiene events at the point of care. Hand hygiene at the point of care may help improve compliance with hand hygiene procedures because the hand hygiene product is conveniently available at the time of the patient interaction. Hand hygiene at the point of care may further help decrease the amount of time between the hand hygiene event and the patient interaction, thus reducing the amount of time for re-contamination of hands to occur and minimizing the risk of transmission of pathogens to the patient. Detecting and recording each dispense event allows for the capture of real-time or near real-time hand hygiene data for a healthcare facility or other organization in which hand hygiene practices are to be monitored. By enabling convenient placement of hand hygiene product dispensers at or near the point of care, and detecting and recording when hand hygiene products have been dispensed, the incidence of healthcare acquired infections may be reduced and better patient health outcomes may be achieved.

FIG. 1A is a front perspective view of an example dispenser holder 100 and FIG. 1B is a front perspective view of example dispenser holder 100 having an example product dispenser 101 installed therein, in accordance with one or more aspects of the present disclosure. In this example, product dispenser 101 is a manual pump bottle including a pump head or pump actuator 105 and a product bottle 103 forming a reservoir for storing a supply of the product to be dispensed. In some examples, the product to be dispensed may include a liquid, a lotion, a gel, or other viscous fluid. In some examples, the pump bottle may include a foaming pump that mixes liquid product from the reservoir with air to create and dispense the liquid product in the form of a foam. In some examples, the product dispenser 101

To dispense product from product bottle 101, a user depresses pump actuator 105, causing product from the product reservoir to be dispensed from the nozzle of the pump actuator 105. In the examples described herein, product dispenser 101 is shown and described as being a manually actuated pump bottle; however, it shall be understood that the dispenser holder described herein is by way of example only, and that product holder 100 may be adapted for any type, size, shape or configuration of product dispenser, any type, size, shape or configuration of product bottle, reservoir or container, and/or any type, size, shape, or configuration of pump or pump actuator, or any other variations of the product dispenser, and that the disclosure is not limited in this respect. For example, in the examples described herein, dispenser holder 100 is configured for a product bottle including a product reservoir having a generally cylindrical shape and having a generally circular cross section; however, dispenser holder 100 may be configured for product bottle(s) of other types, sizes, shapes or configurations, including square, rectangular, elliptical or any other product bottle geometry, and the disclosure is not limited in this respect.

In addition, although the example product holder 100 will be generally described as a product holder for hand hygiene product dispensers, such as hand soap or sanitizer dispensers, it shall be understood that this description is by way of example only, and that the product holder 100 may be used to hold a product dispenser containing any type of product to be dispensed, including but not limited to personal care products such as shampoo, body lotion, etc., hygiene and/or sanitizing products, such as surface sanitizers and/or cleaning products, etc., and that the disclosure is not limited in this respect.

Referring now to FIGS. 2A-2C in addition to FIGS. 1A-1B, FIG. 2A is a front perspective view of the example dispenser holder 100 of FIGS. 1A-1B, in accordance with one or more aspects of the present disclosure. FIG. 2B is a back perspective view of the example dispenser holder 100, in accordance with one or more aspects of the present disclosure. FIG. 2C is a bottom view of the example dispenser holder 100, in accordance with one or more aspects of the present disclosure.

Dispenser holder 100 includes a dispenser holder body 108 including a sidewall 112 and a backplate 126, a top portion 120, and a dispenser holder sensor module indicated generally by reference numeral 124. A front surface of sidewall 112 may be concave to at least partially receive a product dispenser, such as the reservoir portion of a manual pump bottle-type product dispenser 101 as shown in FIG. 1. A bottom portion of sidewall 112 may extend generally forwardly to form interior sidewalls 128 that help to retain product dispenser 101 within dispenser holder 100. Top portion 120 includes first and second arms 102A and 102B, respectively, extending outwardly relative to sidewall 112 of dispenser body 108. In this example, first and second arms 102A and 102B curve inwardly toward the center of dispenser holder 100 to form a generally C-shaped collar forming a receiving area 106. Receiving area 106 is sized to receive at least a portion of product dispenser 101, such as the neck of a manual pump bottle 101 containing the product to be dispensed. Top portion 120 is pivotally connected to the sidewall 112 of dispenser holder body 108 by means of a hinge 104 to permit raising and lowering of first and second arms 102A and 102B between a first, lowered position (as shown in FIGS. 2A and 2B) and a second, raised position. In the first, lowered position, arms 102A and 102B secure a product dispenser within dispenser holder 100. When in the second, raised position, arms 102A and 102B permit removal from and/or replacement of a product dispenser into the dispenser holder 100.

A base 118 is sized to fit within interior sidewalls 128 of bottom portion of sidewall 112 and is configured to support a product dispenser 101 installed in dispenser holder 100. When properly installed into dispenser holder 100, a product dispenser, such as a manual pump bottle 101, is held in position by first and second arms 102A and 102B, interior sidewalls 128 and base 118. One or more removable shims that fit within the collar formed by first and second arms 102A and 102B may also be included to provide a good fit for multiple sizes, shapes, or types of product dispensers. Base 118 and/or sidewalls 128 of base portion 124 may also be sized and/or shaped so as to fit one or more different sizes or shapes of product dispensers, or multiple bases or base inserts may be provided, each configured to hold a differently sized or shaped product dispenser.

Dispenser holder body 108 may be adapted to hold various types of product dispensers, and the size and shape of the dispenser holder body may be changed to suit those various types of product dispensers, including manual pump bottles, trigger sprayer bottles, pump sprayers, pressure sprayers, canisters, containers that dispense or contain cleansing and/or sanitizing wipes, etc. The product dispenser and the corresponding shape(s) (e.g., cross section) of the product holder may be round as shown in the examples herein, or may be square, rectangular, or any regular or irregular shape. It shall therefore be understood that the disclosure is not limited in these respects.

Dispenser holder 100 further includes an actuation button 142. In this example, actuation button 142 includes two upwardly extending cap portions 142A and 142B that extend through corresponding apertures 125A and 125B in base 118. In this example, actuation button 142 is spring biased such that actuation of a product dispenser (e.g., application of a dispenser actuation force to the product bottle) retained in the dispenser holder 100 causes movement of actuation button 142 resulting in detection of an actuation of the product dispenser. In some examples, detection of actuation of the product dispenser may include closure of an actuation switch, detection of movement of the actuation button(s) 142, optical sensing, capacitive sensing, or other type of actuation sensor for detection of actuation of the product dispenser, forming part of dispenser holder sensor module 124 as described herein further below. Detection of dispenser actuation activates an actuation signal that is received by a processor of dispenser holder sensor module 124, by which dispenser holder sensor module 124 detects the dispense event. Actuation button 142 is further biased with sufficient force such that presence of a product dispenser within dispenser holder does not, by itself, result in detection of a dispenser actuation. The biasing force is designed such that neither an empty product dispenser nor a full product dispenser will apply sufficient downward force at a resting steady state to trigger activation of the actuation signal. Upon release of the dispenser actuation force, the biasing force returns the actuation button 142 to the resting state.

As shown in FIGS. 2B and 2C, both back plate 126 and base plate 134 include an aperture 130, 140, respectively. Each aperture 130, 140 forms part of a releasable connection mechanism by which dispenser holder 100 may be connected to a mounting apparatus. In this way, a mounting apparatus may be connected to the back 190 of dispenser holder 100 or to the bottom 150 of dispenser holder 100. In the examples shown and described herein, apertures 130 and 140 are generally octagon-shaped. The octagonal shape of apertures 130 and 140 permits attachment of dispenser holder 100 to a mounting apparatus in multiple orientations, in this example at 45 degree intervals, as will be described herein further below. It shall be understood, however, that apertures 130 and/or 140 may be any n-sided geometric shape, including any regular n-sided polygon, such as a triangle, a square, a rectangle, a pentagon, a hexagon, an octagon, a star polygon, or any other geometry, such as a clover-leaf shape, wheel locks, etc., and that the disclosure is not limited in this respect.

Release tabs 114 and 116 fit within slots which are formed when dispenser holder 100 is fully assembled. Release tabs 114 and 116 slide along and are retained by guide rails within the slots. When assembled, depression of one of release tabs 114 or 116 releases the dispenser holder from the releasable connection to the mounting apparatus. For example, when the back side 190 of dispenser holder is connected to a mounting apparatus, the connection may be released using release tab 114. When the bottom side 150 of dispenser holder is connected to a mounting apparatus, the connection may be released using release tab 116. Further details concerning the dispenser holder and the releasable connection mechanism in accordance with one or more aspects of the present disclosure are described herein further below, and may also be found in U.S. Pat. No. 10,039,423, issued Aug. 7, 2018, which is incorporated herein by reference in its entirety.

Figure 3A:
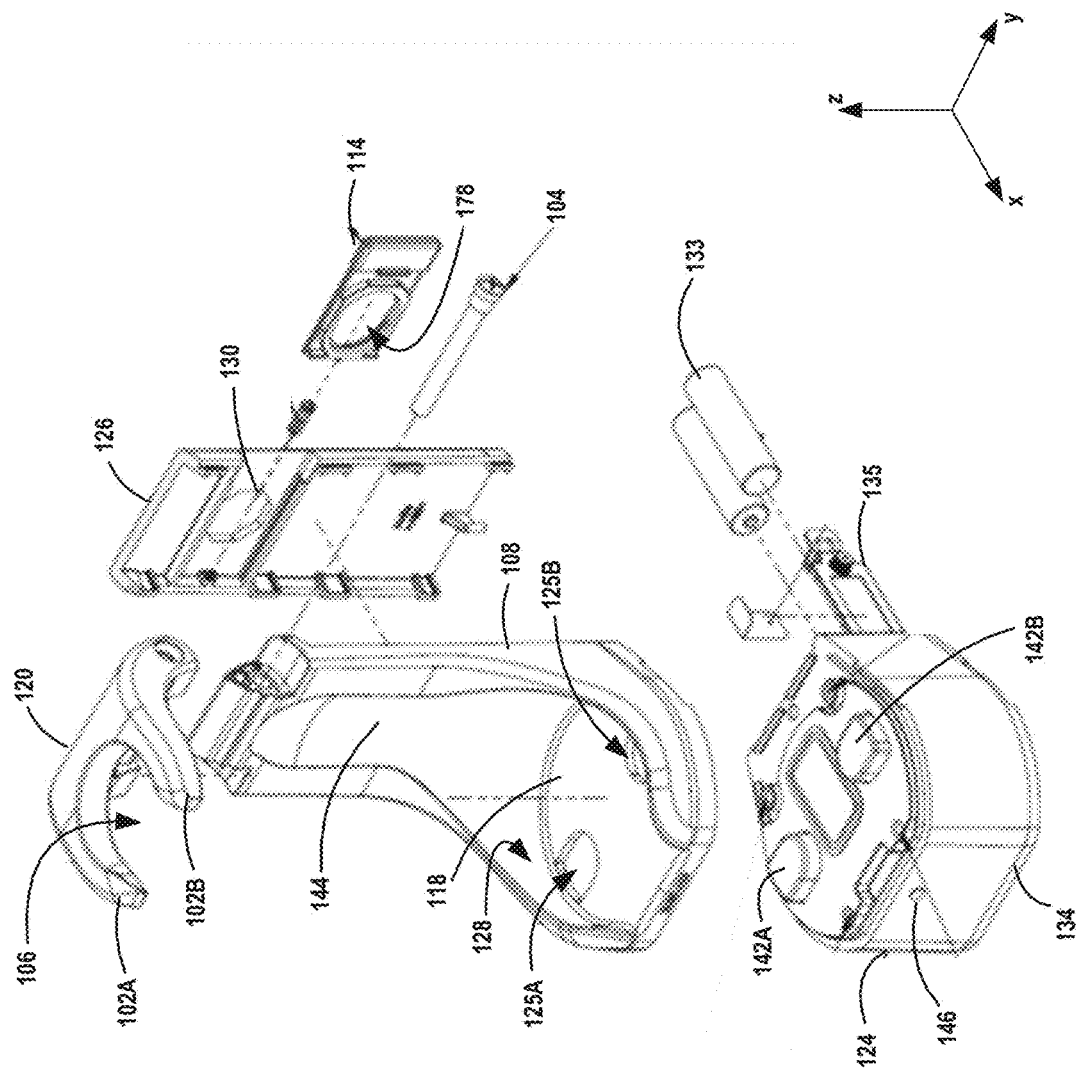
FIG. 3A is a front exploded perspective view of the example dispenser holder of FIG. 1, in accordance with one or more aspects of the present disclosure.
Figure 3B:
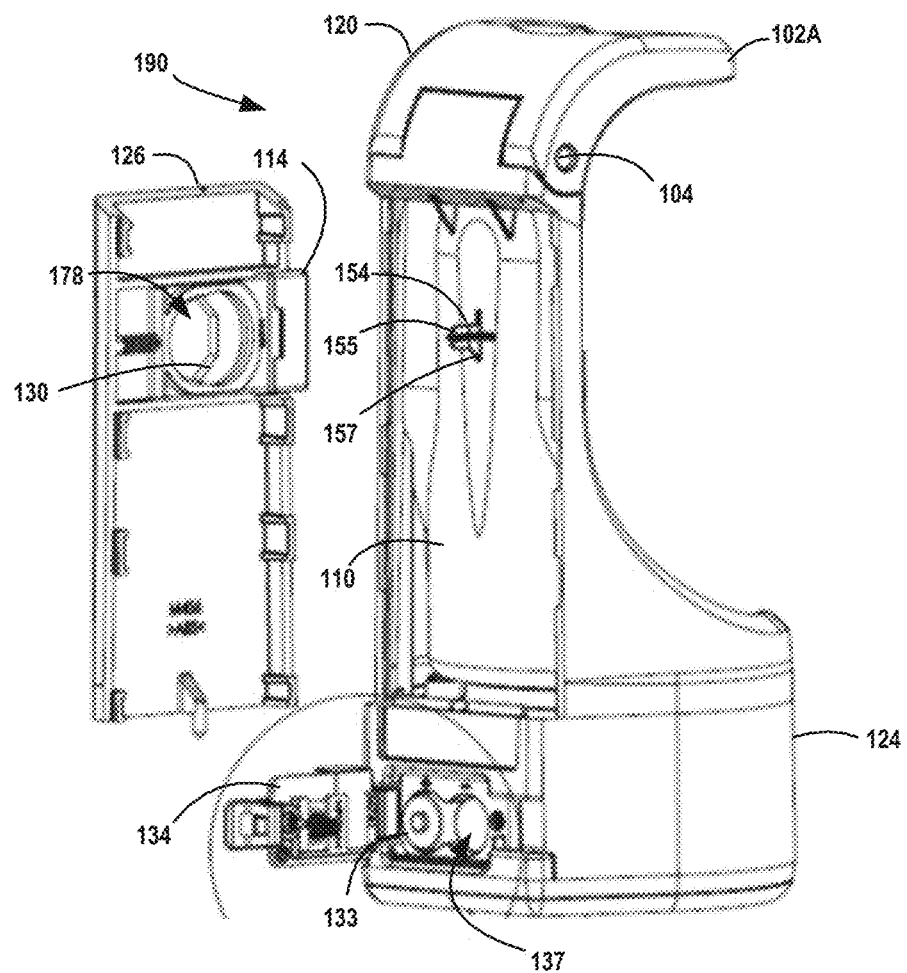
FIG. 3B is a back perspective view of the example dispenser holder of FIG. 1 with the backplate removed and battery door open, in accordance with one or more aspects of the present disclosure.

FIG. 3A is a front exploded perspective view of the example dispenser holder 100, in accordance with one or more aspects of the present disclosure. FIG. 3B is a back perspective view of the example dispenser holder of FIG. 1 with backplate 126 removed and battery door 134 open, in accordance with one or more aspects of the present disclosure. An example x-y-z coordinate system is shown in FIG. 3A for purposes of illustration. In this example, an lateral or x-direction extends through front and back sides of product holder 100, an longitudinal or y-direction extends through left and right sides of product holder 100, and an axial or z-direction extends through top and bottom sides of product holder 100.

A back surface 110 of sidewall 112 includes a first alignment projection 154. Bottom surface of base plate 118 includes a second alignment projection 144 (see FIG. 2C). For each projection 154, 144, the diameter of the base 157, 147, is relatively wider than the diameter of the tip 155, 145. The purpose of tapered projections 154, 144 is to help guide and align the mating halves of the releasable connection as the dispenser holder 100 is loaded onto a mounting apparatus, as further described herein below.

A battery compartment 137 in the dispenser holder sensor module 124 is accessed via a battery door 135 and is sized to receive one or more batteries 133 that provide power to the electronic components of dispenser holder sensor module 124. In this example, battery door 135 is hinged to provide swinging access to the battery compartment. Battery door 135 also includes a latch that secures closed to body. In some examples, battery door 135 may include a thumb screw that further secures it closed to the sensor module body. Battery door 135 may also include battery contacts such that sensor module 124 can only be powered when battery door 135 is closed (i.e., when the circuit is closed).

Figure 4A:
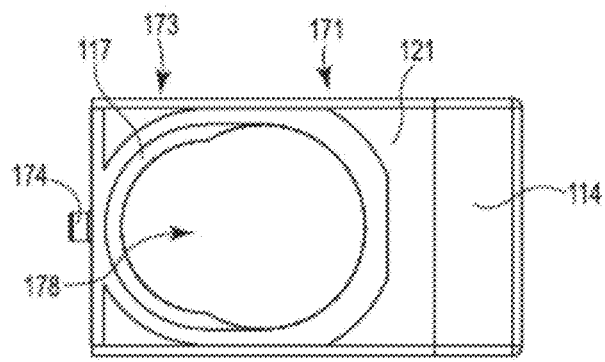
FIGS. 4A and 4B are top and bottom views, respectively, of an example release tab.
Figure 4B:
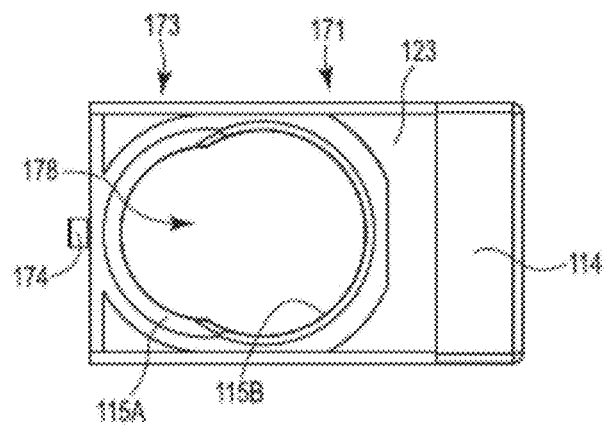

FIGS. 4A and 4B are top and bottom views, respectively, of an example release tab, such as release tab 114. It shall be understood that any other release tabs on dispenser holder 100, such as release tab 116, may have the same design specifications as those shown in FIGS. 4A and 4B. Example release tab 114 includes a top surface 121, a bottom surface 123, aperture 178, and post 174. Aperture 178 is asymmetrical in the sense that aperture 178 includes a first, wider side 171 that is relative wider than a second, narrower side 173. On the bottom surface 123 of release tab 114, a tapered wall 115 is provided around at least a portion of the perimeter of aperture 178. On the top surface 121 of release tab 114, a locking edge 117 is provided on at least a portion of the circumference on second, narrower side 173 of aperture 178. Tapered wall 115 and locking edge 117 cooperate with a mating half of the releasable connection to provide for auto-loading of the dispenser holder onto a mounting apparatus, as further described herein below.

When assembled, the back side surface 110 of sidewall 112 is visible through aperture 130 of back plate 126 (see FIG. 2B). Projection 154 is also visible through aperture 130 of back plate 126. Projection 154 extends outwardly from the back side surface 110 of sidewall 112 and is substantially concentrically aligned with aperture 130. Projection 154 and aperture 130 comprise a first connector clip indicated generally by reference numeral 192. First connector clip 192 is configured to releasably connect with a corresponding mating attachment post provided by a mounting apparatus, as shown and described below.

Similarly, projection 144 is also visible through aperture 140 of base plate 134 (see FIG. 2C). Projection 144 extends outwardly from the bottom surface of base 124 and is aligned substantially in the center of aperture 140. Aperture 140 and projection 144 comprise a second connector clip indicated generally by reference numeral 194. As with first connector clip 192, second connector clip 194 is configured to releasably connect with a corresponding mating attachment post provided by a mounting apparatus, as shown and described below.

First connector clip 192 and second connector clip 194 thus provide alternative connection options that provide flexibility in mounting of the dispenser holder in a wide variety of environments and onto a wide variety of support objects. For example, the mounting apparatus may include a mounting bracket or clamp configured for mounting to a support object including any flat, curved, or irregular surface, such as a wall, a table, a counter top, a cabinet, a shelf, a cart, a pole, a mobile workstation, a column, etc.

For example, dispenser holder may be mounted on a support object, such as a wall, cabinet, pole, post, or other substantially vertical support object using first connector clip 192. As another example, dispenser holder 100 may be mounted on a counter, shelf, medical cart, table, or other substantially horizontal support object using second connector clip 194. In addition, the octagonal geometry of apertures 130 and 140 provide for rotatable mounting of dispenser holder at 45 degree intervals, as further described herein below, thus allowing dispenser holder 100 to be mounted on support objects that are not substantially vertical or horizontal while still maintaining the dispenser holder, and thus the product dispenser itself, in a substantially upright position for dispensation of the product.

Figure 5:
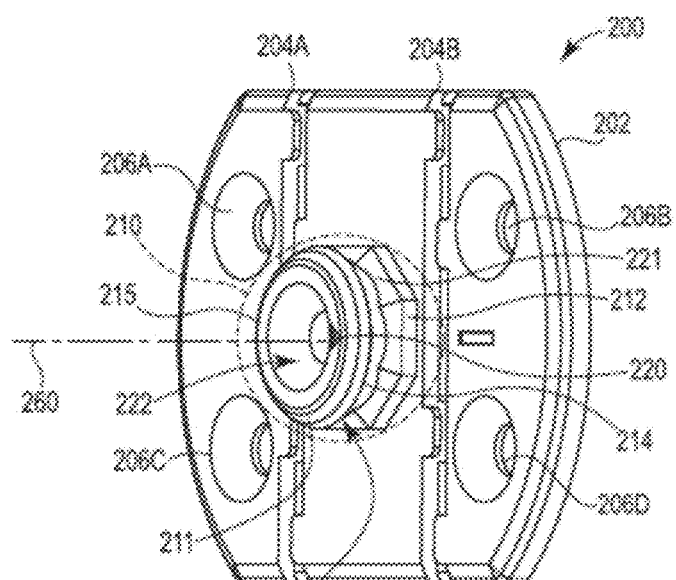
FIG. 5 is a perspective view of an example mounting bracket, in accordance with one or more aspects of the present disclosure.

FIG. 5 is a perspective view of an example mounting bracket 200 by which dispenser holder 100 may be mounted to a variety of support objects. Mounting bracket 200 includes a base plate 202 and an attachment post indicated generally by reference numeral 210. In this example, base plate 202 includes one or more screw holes 206A-206D for screw mounting the mounting bracket 200 to a support object, such as a wall, table, counter, cabinet, or other substantially flat surface. Base plate 202 also includes one or more channels 204A-204B by which mounting bracket 200 may be attached to a support object using one or more cable or zip ties, straps or other type of mechanical fastener. Mounting bracket 200 may also be adhesively mounted to any substantially flat surface.

Base plate 202 may also include one or more hinges that permit mounting bracket 200 to conform to additional contoured surfaces, such as around corners or on rounded surfaces. The hinges may be, for example, a thin flexible hinge or flexible bearing made from the same material as the base plate 202. The hinge may be a living hinge produced in an injection molding operation that creates the hinge and the base plate 202 at one time and as a single piece. For example, base plate 202 may be thinned or cut along one or more of channels 204 to allow the rigid sections of base plate 202 to bend along the line of the hinge. In another example, the hinge may be formed of some other flexible substance and attached to the pieces of the base plate 202 in the desired location to form a conformable mounting bracket 200.

Attachment post 210 includes a base portion 212 and a post portion 214. Post portion 214 further includes a cap 215 and a shaft extending from the cap and defining a center longitudinal axis 260 for the attachment post 210. A top side of cap 215 includes a tapered edge 211 and a bottom side of cap 215 provides a locking surface 217. In this example, base portion 212 includes tapered shoulders 221 and has complementary geometry to the geometry of apertures 130/140. In some examples, the base portion 212 may have the same general geometry as apertures 130/140. To that end, in this example, base portion 212 is substantially octagonal in shape. In general, base portion 212 is sized and shaped to fit within apertures 130 and 140 of dispenser holder 100 such that dispenser holder 100 may be not be rotated around the longitudinal axis 260 once the dispenser holder is loaded onto attachment post 210. As discussed above, although apertures 130 and 140 and base portion 212 of attachment post are described as being octagonal in shape, it shall be understood, however, that apertures 130 and/or 140 and base portion 212 of attachment post 210 may be any n-sided geometric shape, including any regular n-sided polygon, such as a triangle, a square, a rectangle, a pentagon, a hexagon, an octagon, a star polygon, or any other shape, such as clover-leaf shape, wheel lock or any other geometry, and that the disclosure is not limited in this respect. In addition, although the apertures and attachment posts are shown in these examples as having the same geometry, they may have different but complementary geometries, and again the disclosure is not limited in this respect. In some examples, complementary geometries include geometries that are sized and shaped to fit within one another and provide the locking function in one or more orientations as described herein.

Base portion 212 and post portion 214 may be integrally molded with base plate 202 to form a single piece. Attachment post 210 further includes a bore 222 extending through the center longitudinal axis 260 of base portion 212 and post portion 214, and in this example also extends through base plate 202. Bore 222 is sized to receive one of projections 144 and 154 of connector clips 194 and 192, respectively. As mentioned above, octagonal base portion 212 and octagonal apertures 130, 140 provide for mounting of dispenser holder 100 at 45 degree intervals without repositioning of mounting bracket 200. This helps to provide flexible mounting options for the dispenser holder on a wide variety of support objects.

Figure 6:
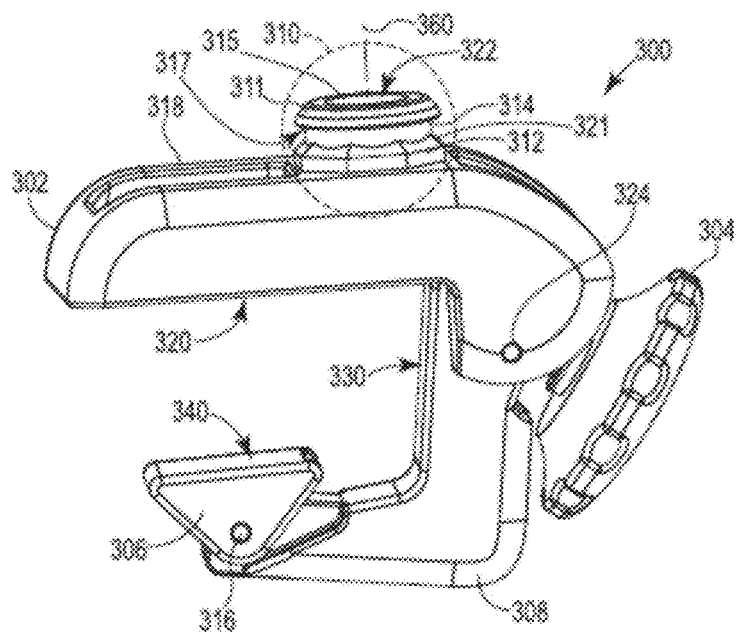
FIG. 6 is a perspective view of an example mounting clamp, in accordance with one or more aspects of the present disclosure.

FIG. 6 is a perspective view of an example mounting clamp 300 in accordance with one or more aspects of the present disclosure. Mounting clamp 300 includes a first jaw 302 having a first inward clamping surface 320, an L-shaped second jaw 308 having a second inward clamping surface 330, and a pivotable tip 306 having a third inward clamping surface 340. First jaw 302 further includes an attachment post 310 extending outwardly away from a top surface 318. Attachment post 310 includes a base portion 312 and a post portion 314. Post portion 314 further includes a cap 315 and a shaft extending from the cap and defining a center longitudinal axis 360 for the attachment post 310. A top side of cap 315 includes a tapered surface 311 and the bottom side of cap 315 provides a locking surface 317.

Attachment post 310 includes a base portion 312 and a post portion 314. Post portion 314 further includes a cap 315 and a shaft extending from the cap and defining a center longitudinal axis 360 for the attachment post 310. A top side of cap 315 includes a tapered surface 311 and the bottom side of cap 315 provides a locking surface 317. Base portion 312 includes tapered shoulders 321 and has the same general geometry as apertures 130/140. To that end, in this example, base portion 312 is substantially octagonal in shape. In general, base portion 312 is sized to fit within apertures 130 and 140 of dispenser holder 100 such that dispenser holder 100 may be not be rotated around the longitudinal axis 360 once the dispenser holder is loaded onto attachment post 310. As discussed above, although apertures 130 and 140 and base portion 312 of attachment post are described as being octagonal in shape, it shall be understood, however, that apertures 130 and/or 140 and base portion 312 of attachment post 310 may be any n-sided geometric shape, including any regular n-sided polygon, such as a triangle, a square, a rectangle, a pentagon, a hexagon, an octagon, a star polygon, or any other multi-faceted or n-sided polygon, and that the disclosure is not limited in this respect. Base portion 312 and post portion 314 may be integrally molded with first arm 302 to form a single piece. Attachment post 310 further includes a bore 322 extending through the center of base portion 312 and post portion 314, and in this example also extends through the top surface 318 of first jaw 302. Bore 322 is sized to receive one of projections 144 and 154 of connector clips 194 and 192, respectively. Attachment post 310 of mounting clamp 300 is of substantially the same geometry and dimensions as attachment post 210 of mounting bracket 200, and thus is similarly configured to releasably attach to one of connector clips 192 and/or 194. As mentioned above, octagonal base portion 312 and octagonal apertures 130, 140 provide for mounting of a dispenser holder 100 at 45 degree intervals without repositioning of mounting clamp 300. This helps to provide flexible mounting options for the dispenser holder on a wide variety of support objects.

First jaw 302 of mounting clamp 300 is pivotally attached at a proximal end to a proximal end of L-shaped second jaw 308 by means of an adjustable hinge 324. A thumb knob 304 permits pivotal adjustment of hinge 324 to open and close first and second jaws 302, 308. Thumb knob 304 may operate by means of a threaded screw adjustment or other mechanism for thumb knob adjustment. Pivotable tip 306 is pivotally attached to a distal end of second jaw 308 by hinge 316. The combination of first clamping surface 320, second clamping surface 330, and third clamping surface 340 provide for 2-point parallel clamping of surfaces such as tables and countertops, and also provides for 3-point clamping of rounded surfaces such as poles.

When mounting to a counter, ledge, or table, for example, the first clamping surface 320 and the third clamping surface 340 may engage the opposed top and bottom surfaces of the table. As another example, when mounting to a pole, bedrail, cart handle, IV pole, etc., the first clamping surface 320, second clamping surface 340, and third clamping surface 340 may provide three points of contact with the pole. The 3-points of contact may provide better clamping retention on poles and/or other rounded support objects, and may help to reduce spinning of the mounting clamp 300 around and/or down a pole, and thus reduce undesirable movement of any dispenser holder 100 mounted to the mounting clamp.

First, second, and/or third clamping surfaces 320, 330, and 340, respectively, may be ridged, grooved, or otherwise textured to provide an improved grip with a support object. Alternatively, the first, second, and/or third clamping surfaces 320, 330, and 340, respectively, may include a tacky surface layer, such as rubber, or other means of providing an improved grip.

Figure 7:
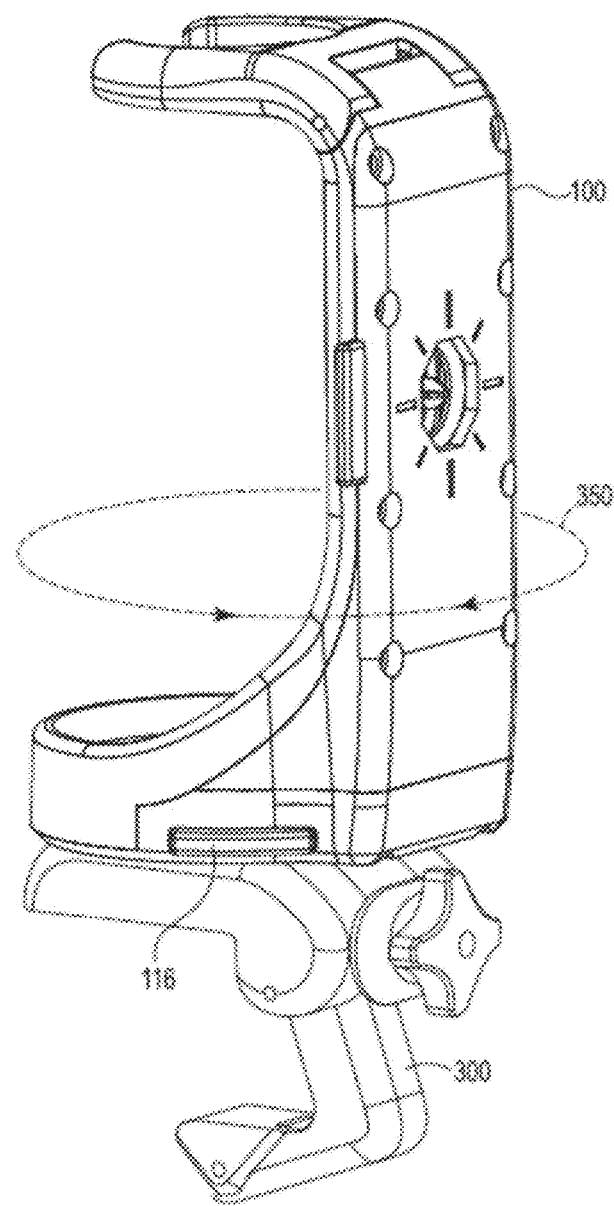
FIG. 7 is a perspective view of an example dispenser holder of FIGS. 1 and 2 attached to the example mounting clamp of FIG. 6.

FIG. 7 is a perspective view of an example dispenser holder 100 attached to the example mounting clamp of FIG. 6. In this example, dispenser holder 100 is releasably connected to attachment post 310 of mounting clamp 300 using second connector clip 194 located on the bottom side of dispenser holder 100. In this configuration, dispenser holder 100 may be mounted at 45 degree intervals around the axis 360 of attachment post 310 (see FIG. 6) as indicated by arrows 350. In another example, dispenser holder 100 may be releasably connected to mounting clamp 300 using first connector clip 192. In another example, dispenser holder 100 may be releasably connected to a mounting bracket 200 using first connector clip 192 or second connector clip 194. In any of these configurations, dispenser holder may be mounted at 45 degree intervals around the axis 360 of attachment post 310 of mounting clamp 300 or axis 260 of attachment post 210 of mounting bracket 200.

In the configuration of FIG. 7, dispenser holder 100 may be releasably detached from mounting clamp 300 using release tab 116. Actuation of release tab 116 releases connector clip 194 from attachment post 310 of mounting clamp 300, thus permitting dispenser holder 100 to be removed from the mounting clamp 300. Dispenser holder 100 may then be reattached at a different 45 degree orientation using connector clip 194 and attachment post 310, may be attached to mounting clamp 300 using first connector clip 192, or may be attached to a different mounting clamp or mounting bracket using either of first connector clip 192 or second connector clip 194.

FIG. 8 is an interior view illustrating the fitting of a mounting bracket 200 and back plate 126 of a dispenser holder 100. In this example, base plate 202 of mounting bracket 200 may be attached to a suitable substantially flat surface. Release tab 114 is positioned to slide within guiderails 164 of back plate 126. A spring 226 is received on a first end by post 170 of back plate 126 and on a second end by post 174 of release tab 114 (posts 170 and 174 not visible in FIG. 8). FIG. 8 also shows octagonal aperture 130 that forms a part of first attachment clip 192 on the back side of dispenser holder 100. Octagonal post base 212 and attachment post 214, and bore 222 are also shown in FIG. 8. Octagonal post base 212 of mounting bracket 200 is fit within octagonal aperture 130 when dispenser holder is attached to mounting bracket 200.

FIG. 8 also illustrates asymmetrical aperture 178 of release tab 114. Release tab 114 is slidably moveable along guiderails 164 to provide a releasable connection between a mounting apparatus, such as mounting bracket 200 shown in FIG. 8, and dispenser holder 100. FIG. 8 shows release tab 114 in the engaged position in which the narrow end of asymmetrical aperture 178 is held in place in the locked or engaged position underneath attachment post 214. Release tab 114 is held in place by a biasing force provided by spring 226. When release tab 114 is depressed in the direction indicated by arrow 370, the wider side of aperture 178 is moved over attachment post 214, thus releasing the corresponding attachment clip 192 from attachment post 214, and permitting dispenser holder 100 to be detached from mounting bracket 200. The release tab 114 is similarly moveable to provide a releasable connection between dispenser holder 100 and any other type of mounting apparatus, such as mounting clamp 300.

Similarly, release tab 116 (see FIGS. 1 and 2) is moveable along guide rails 166 to provide a releasable connection between dispenser holder 100 and a mounting apparatus, such as a mounting bracket 200 or a mounting clamp 300.

FIG. 9 is a side cross-sectional view of a dispenser holder 100 releasably connected to a mounting bracket 200. Mounting plate 202 of mounting bracket 200 includes hexagonal post base 212, attachment post 214, and bore 222 extending through the center of hexagonal post base 212 and attachment post 214. Dispenser holder 100 includes projection 154 extending outwardly from the back surface 110 of sidewall 112 (not shown in FIG. 9). Dispenser holder 100 further includes back plate 126 having octagonal aperture 130, guiderails 164 and release tab 114.

As described above, attachment clips 192/194 are designed for auto-loading of dispenser holder 100 onto a mounting apparatus. Specifically in this example, when dispenser holder 100 is not connected with a mounting apparatus, release tab 114 is maintained in a locked position by a spring force, such as provided by spring 226 in FIG. 8. To load the dispenser holder onto a mounting apparatus, attachment clip 192 or 194 is positioned proximate an attachment post (such as attachment posts 210 or 310) of the mounting apparatus. The user may then push down on the dispenser holder in the direction indicated by arrow 213. Tapered tip 155 of alignment projection 154 cooperates with tapered inner sidewall 225 of bore 22 to guide alignment projection 154 into bore 222 and thus help to align aperture 130 over post base 212 and align post 214 so as to be substantially concentric on a tapered wall 115A on the locking side 173 (the narrow end in this example) of aperture 178.

The tapered wall indicated by reference numerals 115A and 115B around at least a portion of an inner perimeter of aperture 178 cooperates with top tapered edge 211 of cap 115 so as to cause release tab 114 to slide within guiderails 126 toward an unlocked position in which the first, unlocking side 171 (the wider end in this example) of aperture 130 is positioned over cap 215 of attachment post 210. The translational motion of the release tabs within guiderails 126 is substantially perpendicular to the mating force applied by the user and is provided by the chamfered interface of the two components (tapered wall 114 of aperture 178 and the tapered top edge 211 of cap 115).

The dispenser holder may be rotated by the user before pushing the dispenser holder onto the attachment post so as to align the shape of aperture 130 with the shape of post base 212 in a selected one of the one or more orientations defined by the shape of post base 212 and aperture 130.

The dispenser holder may then be further pushed in the direction indicated by arrow 213 until the locking surface 117 of release tab 114 is positioned below the locking surface 217 of cap 215. Release tab 114 is then biased by spring 226, causing release tab 114 to slide along guiderails 126 toward the locked position in which the second, locking (narrower) end of aperture 130 is positioned under cap 215, and locking surface 117 of release tab 114 engages the locking surface 217 of cap 215, as shown in FIG. 9, thus locking dispenser holder 100 to attachment post 210 of the mounting apparatus and preventing its removal therefrom.

During the auto-loading process, projections 154 and 144 may help to counteract the opposing translational force of the spring so as to smoothly guide post 214 to the locking surface 117 instead of being misguided to the opposing side of the spring and hung up on the side wall of aperture 130.

As shown in FIG. 9, when attachment clip 192 formed by projection 154 and hexagonal aperture 130 is positioned for releasable connection with attachment post 210 of mounting bracket 200, octagonal post base 212 is received within octagonal aperture 130, and projection 154 is received by bore 222. Tapered wall 115 of release tab 114 is positioned proximate shoulder 221 of post base 212. Base portion 147 of tapered projection 154 is positioned proximate the tapered sidewall 225 of bore 222. Locking surface 117 on the narrower end of aperture 178 of release tab 114 is positioned below the locking surface 217 of cap 215, thus locking dispenser holder to mounting plate 202. Depression of release tab 114 in the direction indicated by arrow 370 in FIG. 1 causes release tab 114 to slide along guiderails toward the unlocked position, in which the wider side of aperture 178 is positioned over attachment post 214. The wider end of aperture 178 is relatively wider than the widest diameter of cap 215 of attachment post 214, thus permitting dispenser holder to be removed from mounting bracket 200.

Figure 10B:
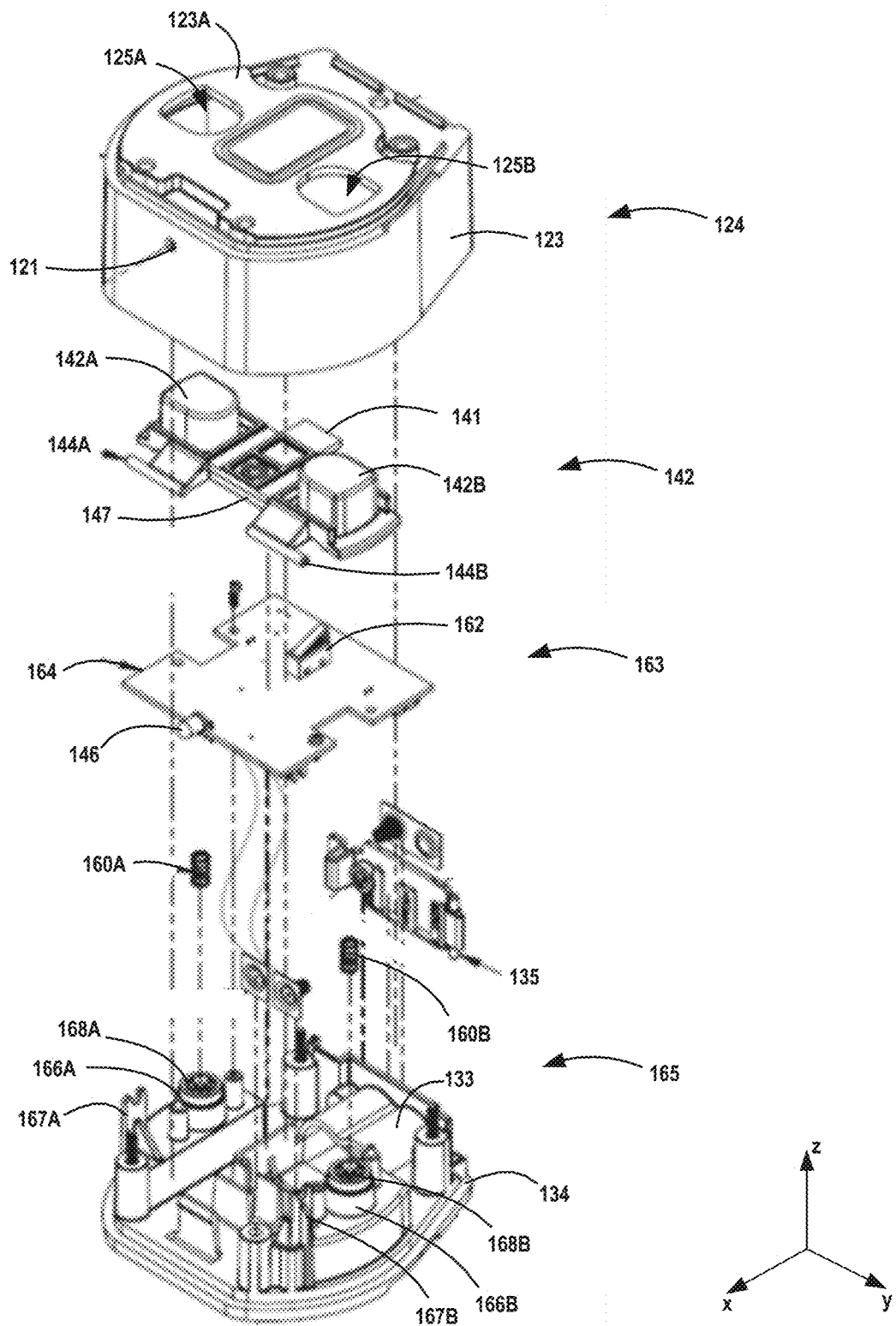
FIG. 10B shows an exploded view of the example dispenser holder sensor module of FIG. 10A, in accordance with one or more aspects of the present disclosure.

FIG. 10A shows a front perspective view of an example dispenser holder sensor module 124, in accordance with one or more aspects of the present disclosure, and FIG. 10B shows a front exploded view of the example dispenser holder sensor module of FIG. 10A, in accordance with one or more aspects of the present disclosure. FIG. 10C shows a cross-sectional side view of module cover 123, and FIG. 10D shows a back perspective view of module body 165, all of the example dispenser holder sensor module 124, in accordance with one or more aspects of the present disclosure. Example x-y-z coordinate system (the same as shown in FIG. 3A) is shown in FIG. 10B for purposes of illustration.

Dispenser holder sensor module 124 includes a module cover 123, an actuation button 142, a circuit board 163, and a module body 165. In this example, module cover 123 includes a top surface 123A having first and second apertures 125A and 125B. Module cover 123 further includes a front surface 123B having a window 121 through which a visual indicator, such as an LED 146, is viewable by a user.

Figure 11A:
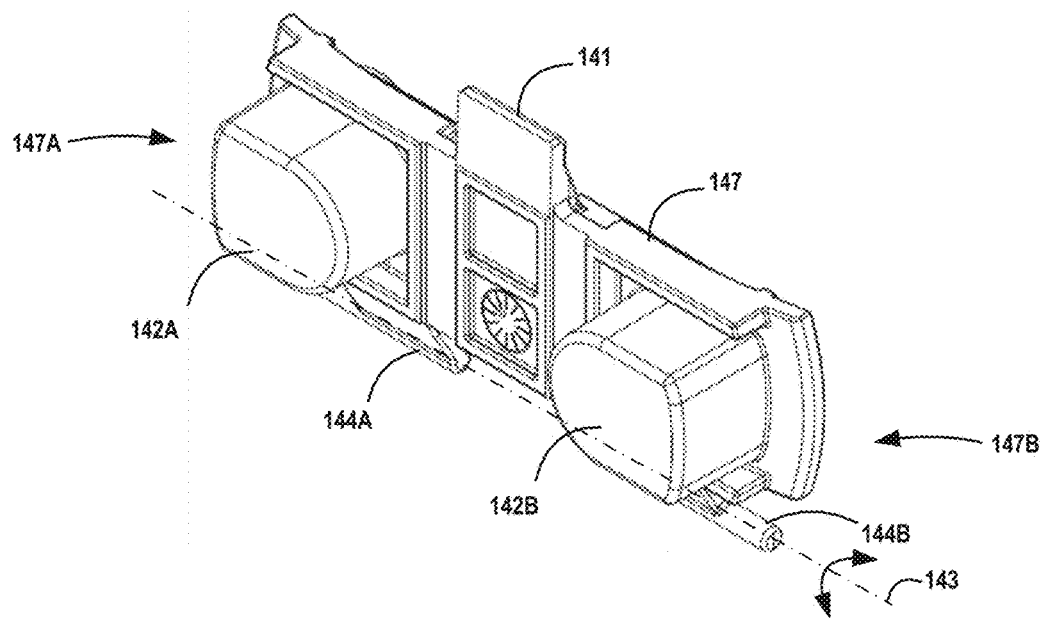
FIG. 11A shows a perspective view of actuation button, in accordance with one or more aspects of the present disclosure.
Figure 11B:
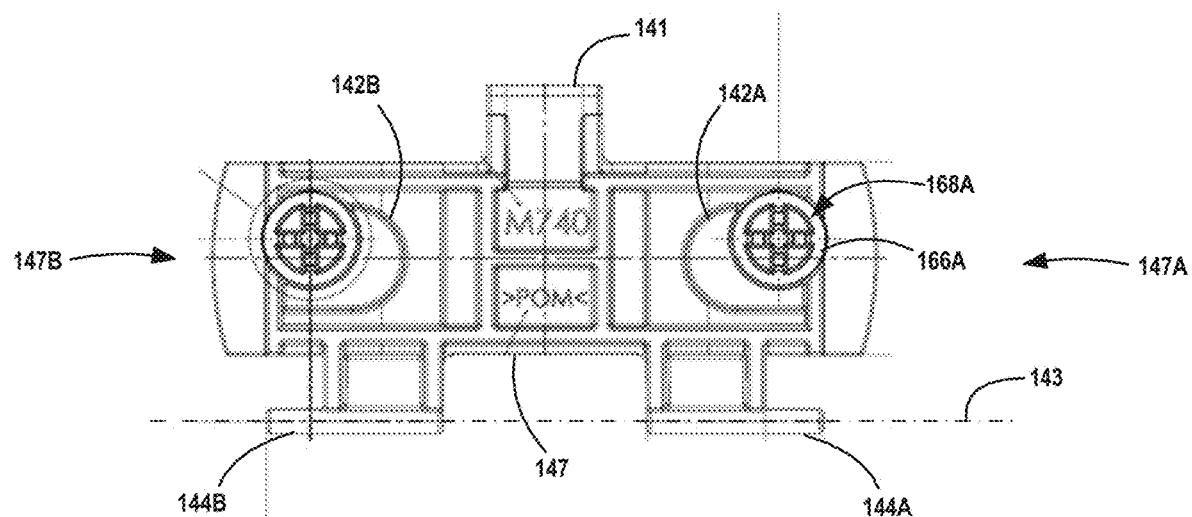
FIG. 11B shows a bottom view of actuation button, in accordance with one or more aspects of the present disclosure.

Actuation button 142 includes a main body portion 147 and two upwardly extending cap portions 142A and 142B extending upwardly (e.g., in the z- or axial direction) from a top side of main body portion at first and second ends 147A, 147B, of main body portion, respectively. Additional views of actuation button 142 are shown in FIGS. 11A and 11B. FIG. 11A shows a perspective view of actuation button 142 and FIG. 11B shows a bottom view of actuation button 142, in accordance with one or more aspects of the present disclosure.

Actuation button 142 further includes a rearwardly extending actuation tab 141. In this example, the actuation tab 141 extends rearwardly (i.e., in the x- or lateral direction) from the center of main body portion 147. Actuation button 142 further includes at least one hinge pin 144 extending from one side of main body portion 147. In this example, actuation button 142 includes first and second hinge pins, 144A and 144B respectively, extending forwardly from a front side of main body portion 147 at first and second ends of main body portion, respectively. In other examples, first and second hinge pins 144A and 144B may form a single hinge pin 144. An axis 143 of hinge pins 144A/144B extends substantially parallel to a lengthwise or longitudinal dimension of main body portion 147. In this example, therefore, axis 143 is substantially parallel to the longitudinal or y-axis of dispenser holder 100. In some examples, actuation button is formed of a single piece of injection molded plastic or other rigid material.

Figure 12:
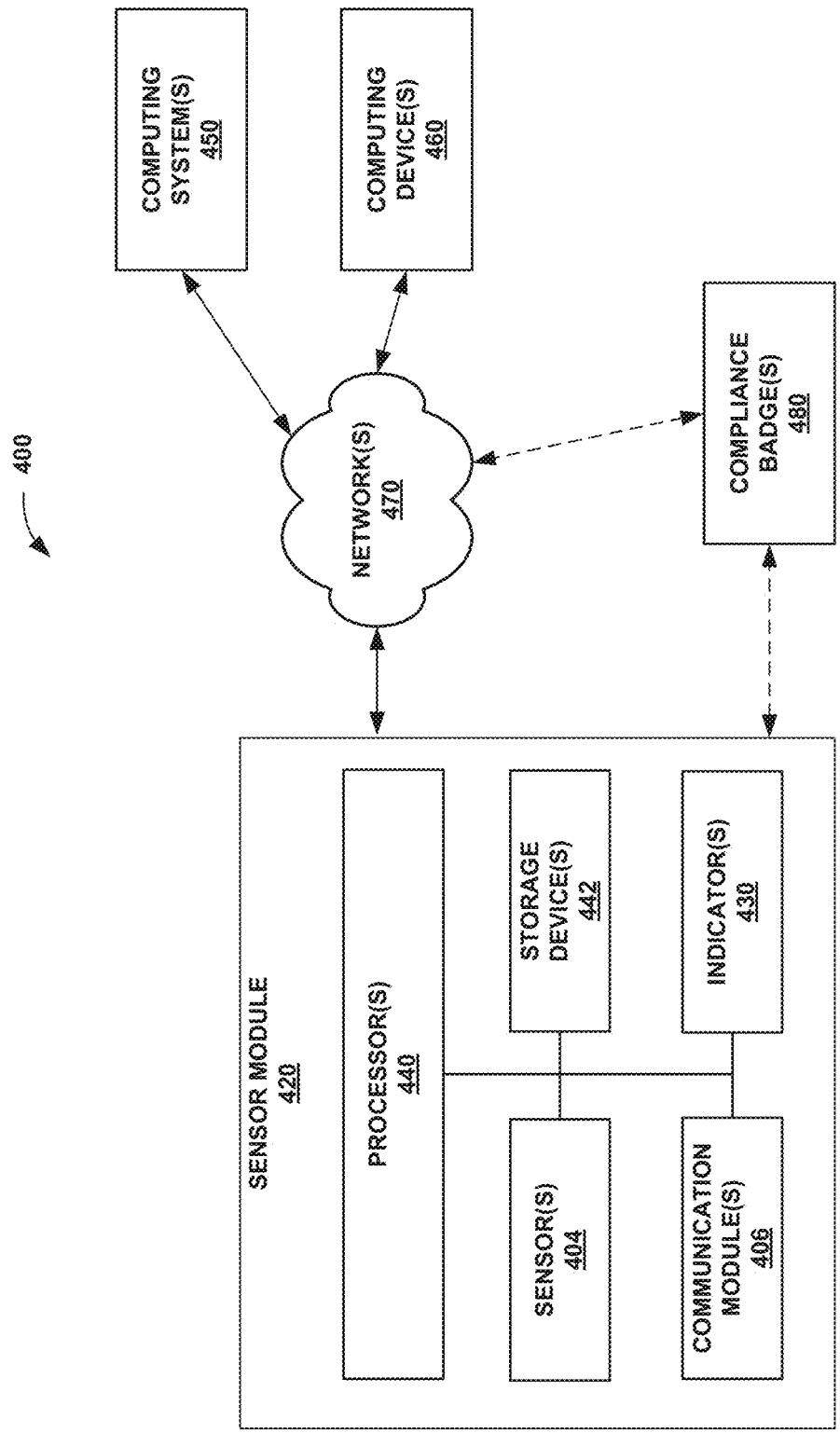
FIG. 12 is a block diagram of an example dispenser holder sensor module and an environment in which the sensor module may be used to communicate data concerning product dispenser actuations.

In this example, circuit board module 163 includes actuation sensor 162 and LED indicator 146. Circuit board module 163 may also include one or more electronic components, such as any one or more of the electronic components as shown in FIG. 12, for example.

In this example, actuation sensor 162 is implemented using a mechanical switch including a lever actuator and spring mechanism. However, it shall be understood that actuation sensor 162 could be implemented using any other type of sensor capable of detecting actuation of the product dispenser. In some examples, the actuation sensor 162 need not be located as shown herein, but could be located in a different position on the circuit board or relative to the other mechanical and/or electronic components depending upon the particular implementation. For example, an actuation sensor may be implemented using a different type of mechanical switch that is actuated by closing of electrical contacts. As another example, an actuation sensor may be implemented by sensing movement or acceleration of one or more portions of the actuation button 142, such as an accelerometer or an optical sensor. As another example, an actuation sensor may be implemented by detecting a change in force applied to actuation buttons 142, such as a load cell, force transducer, or other force sensing sensor such as a force sensing resistor. As another example, an actuation sensor may be implemented using a force sensing layer in the base of the product holder that detects micro deflection of the base, in which case actuation button 142 may not be necessary. As another example, an actuation sensor may be implemented using any type of device that senses a change in an electric field, such as a capacitive sensor. As another example, where the dispenser holder does not include a base and the product dispenser is instead supported around the neck of the product bottle by the top portion (i.e., first and second arms) of the product holder, a force sensing device(s) may be positioned in and/or around the top portion of the product holder that detects a force applied to the pump of the product bottle.

In general, any type of one or more actuation sensor(s) maybe used, including but not limited to any type of mechanical switch, a reed switch, an accelerometer, a load cell, a force transducer, a force sensing resistor, an optical sensor, a membrane switch, a capacitive sensor, etc. Thus, it shall be understood that although the example shown herein describes an actuation switch 162, that any type of actuation sensor may be used, and that the disclosure is not limited in this respect. The components of dispenser holder 100 may also be implemented using different components selected to form an operable system in combination with the type of actuation sensor, and the disclosure is further not limited in this respect. It shall therefore be understood that although a particular embodiment is shown and described herein, that other implementations selected to accomplish the same or similar functionality (namely, detection of an actuation force applied to a product bottle held in the dispenser holder 100) may also be used, and that the disclosure is not limited in this respect.

In this example, module body 165 includes a bottom plate 134, battery compartment 133 and battery door cover 135. Module body 165 further includes spring seat posts 166A and 166B substantially aligned with cap portions 147A and 147B, respectively. Spring seat posts 166A and 166B each include a top surface forming seats 168A and 168B for a first end of biasing springs 160A and 160B, respectively. The second end of each of biasing springs 160A and 160B seats within the respective cap portions 147A and 147B when dispenser holder sensor module 124 is fully assembled.

Module body 165 further includes hinge posts 167A and 167B extending upwardly from an interior surface of base plate 134. A top end of each of hinge posts 167A and 167B include a recessed knuckle for receipt of one of hinge pins 144A and 144B, respectively. Corresponding recessed knuckles that retain a top side of hinge pins 144A and 144B are located inside module cover 123 (see FIG. 10C). This configuration of hinge pins 144A and 144B and hinge posts 167A and 167B allow actuation button 142 to rotate on axis 143 of hinge pins 167A and 167B. In operation, when an actuation force is applied to cap portions 142A and/or 142B (such as when a user depresses pump 105 of pump bottle 101 to dispense hand hygiene product), actuation button 142 rotates substantially downwardly (clockwise from the viewpoint of FIG. 10B) around axis 143 of hinge pins 167A and 167B. This rotation of actuation button 142 results in actuation tab 141 rotating substantially downwardly thereby closing actuation switch 162 and activating the dispenser actuation signal. At the same time, biasing springs 160A and 160B are compressed. When the actuation force is removed, such as when the user removes their hand from the pump bottle actuator, the biasing springs 160A and 160B resiliently decompress and return to their unbiased state, causing actuation button 142 to rotate substantially upwardly around axis 143 until they reach a rest state. The resting state is determined in part by the biasing force applied by springs 160A and 160B and the weight of the product container retained in the dispenser holder. Springs 160A and 160B have a "loaded" upward force in steady state so that they hold a weighted (fully filled) product dispenser in place at rest, while allowing a dispensing force applied by a human to result in sufficient travel to activate switch 162.

To prevent overtravel of activation button 142, the flat top surfaces of seat posts 166A and 166B serve as a hard stop so that activation button 142 can not rotate any further around axis 143. This hard stop helps ensure that no force/damage is placed upon the activation switch 162 and that springs 160A and 160B are not overcompressed.

In this example, button caps 142A and 142B were selected in a left/right configuration and intended to contact the outer rim of the product bottle, but we are not limited to this configuration. The dimensions of button caps 142A and 142B (e.g., the length and width of the tops of button caps 142A and 142B) were designed with large surface area to ensure there is sufficient contact with the base of a product bottle even with different styles and/or sizes of product bottle.

Referring again to FIG. 2A, in this example, the dimensions (e.g., the height) of button caps 142A and 142B are chosen such that they only slightly protrude from surface 118. Because of this, when a product bottle is placed into the product holder, it almost appears from the user's perspective that the product bottle is resting on surface 118. In this example, therefore, the actuation distance of button 142 around axis 143 is minimized to the extent possible to ensure the product bottle does not greatly move and startle/cause difficulty to the human receiving sanitizer or soap during actuation of the product bottle. In this way, the user's perspective is considered to help ensure the activation detection system had minimal impact on user experience. In addition, in this example, the dimensions of button caps 142A and 142B were selected so as not to be too tall and/or hold the product bottle up too high and therefore did not result in squeezing the product bottle 101 between button caps 142A/142B and collar 120.

Although a specific configuration of the product holder is shown and described herein, it shall be understood that the disclosure is not limited in this respect, and that other variations may also be within the scope of the present disclosure. For example, the product holder may include one, two or more actuation buttons 142. In addition, although two actuation buttons 142A/142B are illustrated herein as being arranged along a line extending in a longitudinal direction (i.e., along a line parallel to a y-axis as defined in FIGS. 3A and 10B, for example), it shall be understood that one or more actuation buttons may be arranged along a line extending in a lateral direction (i.e., parallel to an x-axis) or arranged circumferentially around an axial axis (z-axis), or in any other suitable arrangement. The top surface of the one or more actuation buttons may also be of any suitable shape, dimensions, and/or surface area. In addition, the top surfaces of the one or more actuation buttons may be of the same shape or may be of different shapes.

A configuration such as that shown in FIGS. 10A-10D may be useful in hospital or restaurant settings where monitoring of hand hygiene practices is desired. For example, a hand hygiene product dispenser, such as a manual pump bottle, may be installed in dispenser holder 400. When the pump bottle is actuated by a user, the downward force applied to the manual pump actuator is transferred (at least in part) to the pump bottle. This downward force causes a corresponding movement of actuation button 142, thus closing actuation switch 162 located within dispenser holder sensor module 124 and activating an actuation signal. Dispenser holder sensor module 124 includes processing circuitry that receives the sensed actuation signal and may process the actuation signals in any of a number of ways.

For example, processing circuitry of dispenser holder sensor module 124 may be configured to communicate dispense event data associated with each detected dispense event (that is, each detected dispenser actuation). The communication may be wired or wireless. In some examples, the processing circuitry of dispenser holder sensor module 124 communicates with one or more remote computing devices via one or more local or remote communication networks. In some examples, processing circuitry of dispenser holder sensor module 124 is further configured to communicate with one or more user compliance badges as part of a hand hygiene compliance system.

Processing circuitry of dispenser holder module 124 may further be configured to increment a dispense event count upon each detected dispenser actuation and store a total number of sensed dispenser actuations. As another example, the processing circuitry may be configured to activate a visual indicator, such as an LED indicator, and/or an audible indicator, in response to each detected actuation of the product dispenser. As another example, the processing circuitry may be configured to determine an amount of product remaining in the product bottle and/or determine a number of dispenses remaining in the product bottle. As another example, processing circuitry may be configured to determine when an empty product bottle has been replaced with a different product bottle (e.g., such as replacing an empty product bottle with a full product bottle or switching product bottles from one type of product to another type of product). As another example, the processing circuitry may be configured to determine a number of dispenses remaining before a low battery condition is reached. As another example, the processing circuitry may be configured to determine a current battery status, and to generate a notification concerning the battery status. As another example, the processing circuitry may be configured to communicate the dispense event data and any other relevant data to an external computing device. The dispense event data may include, for example, a date/time stamp associated with the dispenser actuation and/or any of the other information described herein.

FIG. 12 is a block diagram of an example electronic sensor module 420 of a dispenser holder 100 and an environment in which sensor module 420 may be used to communicate data concerning product dispenser actuations in accordance with one or more techniques of the present disclosure. Sensor module 420 may be used to implement the electronic components of dispenser holder sensor module 124 as shown and described herein. As such, one or more components of sensor module 420 may be mounted on a circuit board, such as circuit board 164, and installed within a dispenser holder sensor module housing such as shown in FIG. 10B.

Sensor module 420 includes one or more actuation sensors 404, one or more indicators 430, one or more processor(s) or processing circuitry 440, communication module(s) 406, and one or more storage device(s) 442 (memory). Actuation sensors 404 may include, for example, any type of sensor, switch, or other mechanism capable of detecting actuation of a product dispenser, and that thus detect occurrence of a dispense event. In the example shown in FIG. 10C, sensor 404 is implemented using switch 162.

Sensor module 420 may include one or more communication modules 406 that enable sensor module 420 to communicate with one or more external computing device(s) 460, remote computing system(s) 450, and/or one or more compliance badge(s) 480. Network(s) 470 may include, for example, one or more of a dial-up connection, a local area network (LAN), a wide area network (WAN), the internet, a cell phone network, satellite communication, Bluetooth, Bluetooth Low Energy (BLE), Near Field Communication (NFC), Wi-Fi, or other means of electronic communication. The communication may be wired or wireless. In some examples, sensor module 420 may communicate directly with compliance badges 480 using one or more short range communication protocols such as Bluetooth, Bluetooth Low Energy (BLE), Radio Frequency Identification (RFID), Near Field Communication (NFC), or other means of short range wireless electronic communication.

Storage device(s) 442 include one or more software and/or firmware modules that, when executed by processor(s) 440, cause processor(s) to perform one or more functions associated with the detection of a dispenser actuation and transmission of dispenser data for receipt by one or more computing devices. For example, upon each sensed dispenser actuation, processor(s) 440 of sensor module 420 receives a sensor actuation signal from actuation sensor 404. Processor(s) 440 generates dispense event data including, for example, a date/time stamp associated with when the sensed actuation was received. In some examples, processor(s) 440 attempts to initiate a communication session with a compliance badge in the vicinity of the dispenser holder in order to identify a user with whom to associate the detected dispense event. For example, processor(s) 440 may attempt to communicate with a nearby compliance badge using a form of short range communication. If the attempt is successful and processor(s) 440 successfully establish communication with one of compliance badges 480, processor(s) 440 may receive compliance badge identification information and/or user identification information from compliance badge 480 via the established communication link. Processor(s) 440 may then transmit the dispense event data, including the time/date stamp associated with the dispense event, the received badge identification information and/or user identification information, dispenser/dispenser holder identification information, and/or any other data that may be relevant for monitoring of hand hygiene compliance, status of the hand hygiene product dispenser, and/or status of product bottle in the product dispenser holder for receipt by one or more computing devices, such as computing devices 450 and/or 460.

Processor(s) 440 of sensor module 420 may further be configured to count the number of sensed dispenser actuations. For example, processor(s) 440 may increment a count of detected dispense events stored in data storage 442 each time a dispenser actuation signal is received from one or more of sensor(s) 404. In another example, sensor module 420 may include a counter in addition to or instead of processor(s) 440. As another example, sensor module 420 may be configured to activate one or more indicators 430, such as one or more audible or visual indicators, each time a dispenser actuation is sensed. This may provide audible and/or visual feedback to a user as to whether the dispenser was depressed sufficiently to dispense a desired dosage of hand hygiene product.

As another example, sensor module 420 may be configured to communicate dispense event data corresponding to each sensed dispense event (including the counted number of dispense events or other dispense event data) to an external device or system (such as one or more computing devices 460 and/or computing system 450) via networks 470. The communication may be in real-time or near real-time (e.g., at or near the time of each detected dispense event). In some examples, dispense event data associated with each dispense event detected by sensor module 420 may be stored in storage devices 442. In such examples, the dispense event data may in addition or alternatively be sent at periodic intervals, at one or more scheduled times, or on demand. For example, sensor module 420 may further store and communicate dispense event data corresponding to one or more dispense events periodically (e.g., once per hour, once per day, etc.) or on demand (such as upon receipt of a command from one or more of computing devices 450/460. The dispense event data may include a time stamp indicative of the date and time of the associated dispense event. The dispense event data may further include one or more of a counted number of dispense events, a compliance module battery status, a number of dispenses remaining, a date and/or time that the product bottle was last replaced or refilled, a low battery indicator, a low product indicator, an empty product indicator, an indication that no product bottle is present in the product holder, and/or any other relevant information that may be detected and/or communicated by sensor module 420.

Computing systems 450 may include a local computer configured to receive dispense event data from multiple sensor modules 420 associated with one or more dispenser holders 400 installed in different locations associated with a particular entity, location or site. Computing systems 450 may also include a remote server computer configured to receive dispenser actuation data from multiple facilities, locations or sites. Computing device(s) 460 may include, for example, one or more base stations positioned within a facility or other computing devices configured to receive dispense event data.

In some examples, one or more sensor module(s) 420, computing system(s) 450, computing device(s) 460, and compliance badges 480 may be part of a hand hygiene compliance system that monitors, analyzes, stores, and/or reports data related to hand hygiene compliance. In such examples, each of the plurality of compliance badges 480 may be uniquely associated with an employee of an entity or facility, such as a hospital or other healthcare facility, restaurant, food preparation or processing facility, or other entity in which hand hygiene compliance is to be monitored. Upon detection of a dispenser actuation, sensor module 420 may detect and communicate with a compliance badge 480 located near the dispenser holder sensor module 420. For example, sensor module 420 may communicate with compliance badges 480 using any form of short range wireless communication. Compliance module 420 may further receive user identification information from the detected compliance badge 480 and transmit the user identification information as part of the hand hygiene compliance data associated with the dispense event, thus associating each dispense event with a particular compliance badge and/or user. The transmitted dispense event data may be received by one or more computing devices, such as computing devices 450 and/or 460. Computing device 350 and/or 460 may analyze the dispense event data received from one or more sensor modules 420 to monitor hand hygiene compliance at one or locations associated with an entity.

Example hand hygiene compliance systems in which dispenser holder 400 and dispenser holder sensor module 420 may be used are described in U.S. Pat. No. 8,395,515, issued Mar. 12, 2013, U.S. Pat. No. 8,502,680, issued Aug. 6, 2013, United States Publication No. 2018/0255918, filed Mar. 6, 2018, and United States Publication No. 2020/0205055, filed Dec. 20, 2019, all of which are incorporated herein by reference in their entirety.

In one or more examples, the functions described may be implemented in any combination of processing circuitry, including hardware, software, firmware, or any combination thereof. If implemented in software, the functions may be stored on or transmitted over a computer-readable medium as one or more instructions or code, and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can include RAM, ROM, EEPROM, CD-ROM or other optical disk storage, magnetic disk storage, or other magnetic storage devices, flash memory, or any other medium that can be used to store program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more DSPs, general purpose microprocessors and/or microcontrollers, ASICs, FPGAs, or other equivalent integrated or discrete logic circuitry, as well as any combination of such components. Accordingly, the term "processor," as used herein may refer to any of the foregoing structures or any other structure suitable for implementation of the techniques described herein. In addition, in some aspects, the functionality described herein may be provided within dedicated hardware and/or software modules. Also, the techniques could be fully implemented in one or more circuits or logic elements.

The techniques of this disclosure may be implemented in a wide variety of devices or apparatuses, including a wireless communication device, a microprocessor, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware, and/or any other type or combination of processing circuitry.

Various examples have been described. These and other examples are within the scope of the following claims.

The invention claimed is:

1. A sensor module for a product dispenser holder, the sensor module comprising:
   an actuation sensor that generates a dispenser actuation signal;
   an actuation button comprising:
   a main body portion; and
   at least one cap portion extending upwardly from a top side of the main body portion and sized to extend through at least one aperture in a base of a dispenser holder body of the product dispenser holder, wherein when an actuation force is applied to a pump of a product dispenser held by the dispenser holder body, the pump is actuated to dispense a dosage amount of a product from a product reservoir of the product dispenser and when the actuation force is applied to the pump, a substantially downward force is applied to the at least one cap portion of the actuation button, causing actuation of the actuation sensor to generate the dispenser actuation signal;
   processing circuitry configured to detect a dispense event upon receipt of the dispenser actuation signal;
   a communication module configured to, after the processing circuitry detects the dispense event:
   attempt to communicate with a compliance badge using a short-range wireless communication protocol; and
   if the processing circuitry successfully communicates with the compliance badge, receive identification information from the compliance badge, wherein the identification information includes compliance badge identification information or user identification information,
   wherein the processing circuitry is further configured to generate dispense event data corresponding to the dispense event, and wherein the sensor module is configured to determine at least one or more of an amount of remaining product, an empty product bottle, or a product bottle replacement.

2. The sensor module of claim 1, wherein the short-range wireless communication protocol includes at least one of: Bluetooth, Bluetooth Low Energy (BLE), Radio Frequency Identification (RFID), or Near Field Communication (NFC).

3. The sensor module of claim 1, further comprising a sensor module body forming a lower spring seat,
   wherein the main body portion of the actuation button further includes an upper spring seat on a bottom side of the main body portion; and
   wherein the at least one cap portion is biased by a spring seated between the lower spring seat and the upper spring seat.

4. The sensor module of claim 1, wherein the product dispenser comprises a manual pump bottle.

5. The sensor module of claim 1, further comprising a visual indicator configured to be activated in response to the dispense event.

6. The sensor module of claim 1, further comprising a counter that increments a dispense event count in response to the dispense event.

7. The sensor module of claim 1, wherein the communication module is configured to communicate the dispense event data to a hand hygiene compliance computing system.

8. The sensor module of claim 7, wherein the hand hygiene compliance computing system is configured to analyze dispense event data received from one or more product dispenser holders to monitor hand hygiene compliance of one or more workers associated with a facility.

9. The sensor module of claim 1, wherein the actuation button further comprises a hinge pin extending from a first side of the main body portion configured such that the actuation force applied to the pump of the product dispenser causes the actuation button to rotate on an axis defined by the hinge pin such that the actuation button is displaced downwardly and actuates the actuation sensor to generate the dispenser actuation signal.

10. The sensor module of claim 9, wherein the actuation button includes an actuation tab extending from the main body portion configured such that when the actuation force is applied to the pump, the substantially downward force is applied to the at least one cap portion of the actuation button, causing the actuation tab to rotate substantially downwardly and actuate the actuation sensor to generate the dispenser actuation signal.

11. The sensor module of claim 10, wherein:
the hinge pin is a first hinge pin,
the actuation button further comprises a second hinge pin extending from a second side of the main body portion,
the first hinge pin and the second hinge pin define the axis, the at least one aperture in the base of the dispenser holder body includes first and second apertures;
the at least one cap portion of the actuation button includes first and second cap portions extending upwardly from the top side of the main body portion and sized to extend through the first and second apertures in the base of the dispenser holder body, respectively, and
the actuation tab is configured such that when the actuation force is applied to the pump, the substantially downward force is applied to at least one of the first and second cap portions of the actuation button, causing the actuation button to rotate on the axis defined by the first hinge pin and the second hinge pin causing the actuation tab to move substantially downwardly and depress the actuation sensor to generate the dispenser actuation signal.

12. The sensor module of claim 11, wherein:
the sensor module further comprises a sensor module body that forms a first lower spring seat and a second lower spring seat,
wherein the main body portion of the actuation button further includes a first upper spring seat on a bottom side of the main body portion and a second upper spring seat on the bottom side of the main body portion,
wherein the first cap portion is biased by a first spring seated between the first lower spring seat and the first upper spring seat, and
wherein the second cap portion is biased by a second spring seated between the second lower spring seat and the second upper spring seat.

13. The sensor module of claim 1, wherein the processing circuitry is further configured to store the dispense event data corresponding to the dispense event.

14. The sensor module of claim 1, wherein the actuation sensor includes one of a mechanical switch, a reed switch, an accelerometer, a load cell, an optical sensor, a membrane switch, or a capacitive sensor.

15. The sensor module of claim 1, wherein the at least one cap portion of the actuation button includes two or more cap portions, each of the two or more cap portions extending through a respective aperture in the base of the dispenser holder body.

16. The sensor module of claim 1, wherein the product includes one of a liquid, a lotion, a gel, or other viscous fluid.

17. The sensor module of claim 1, further configured to estimate a number of dispenses remaining before a low battery condition.

18. The sensor module of claim 1, further configured to provide a battery status.

19. The sensor module of claim 1, further configured to provide a battery status notification.

20. The sensor module of claim 1, further configured to provide a low battery indicator.

* * * * *